(12) United States Patent
Zou et al.

(10) Patent No.: US 7,759,547 B2
(45) Date of Patent: *Jul. 20, 2010

(54) METHODS OF PRODUCING AND GROWING PLANTS HAVING IMPROVED PHOSPHORUS UTILIZATION

(75) Inventors: Jitao Zou, Saskatoon (CA); Wenyun Shen, Saskatoon (CA); Wilf Keller, Saskaoon (CA)

(73) Assignee: National Research Council of Canada, Ottawa, Ontario (CA)

( * ) Notice: Subject to any disclaimer, the term of this patent is extended or adjusted under 35 U.S.C. 154(b) by 1138 days.

This patent is subject to a terminal disclaimer.

(21) Appl. No.: 11/122,943

(22) Filed: May 4, 2005

(65) Prior Publication Data
US 2005/0204423 A1 Sep. 15, 2005

Related U.S. Application Data

(63) Continuation-in-part of application No. 10/088,079, filed as application No. PCT/CA00/01096 on Sep. 21, 2000, now Pat. No. 7,112,724.

(60) Provisional application No. 60/155,133, filed on Sep. 22, 1999.

(51) Int. Cl.
A01H 5/00 (2006.01)
C12N 15/82 (2006.01)
(52) U.S. Cl. ........................ 800/295; 800/278; 800/281; 800/306; 800/320.1; 800/320.2; 435/468
(58) Field of Classification Search ....................... None
See application file for complete search history.

(56) References Cited

U.S. PATENT DOCUMENTS

| | | | |
|---|---|---|---|
| 5,210,189 A | 5/1993 | Murata | |
| 5,427,240 A | 6/1995 | Holtkamp | |
| 5,463,175 A * | 10/1995 | Barry et al. | 800/300 |
| 5,516,667 A | 5/1996 | Nishizawa | |
| 5,859,333 A | 1/1999 | Keeling et al. | |
| 6,051,755 A | 4/2000 | Zou et al. | |
| 6,103,520 A | 8/2000 | Topfer et al. | |
| 6,358,716 B1 | 3/2002 | Bulthuis et al. | |
| 7,112,724 B1 * | 9/2006 | Zou et al. | 800/298 |
| 7,351,560 B2 | 4/2008 | Park et al. | |
| 2003/0233675 A1 | 12/2003 | Cao et al. | |
| 2004/0205845 A1 | 10/2004 | Rigierer et al. | |

FOREIGN PATENT DOCUMENTS

| | | |
|---|---|---|
| CA | 2170611 | 3/1995 |
| CA | 2 484 001 | 5/2003 |
| EP | 0 843 007 | 5/1998 |
| EP | 0 843 007 A1 | 5/1998 |
| WO | WO 92/13082 | 8/1992 |
| WO | WO 95/06733 | 3/1995 |
| WO | WO 96/38573 | 12/1996 |
| WO | WO 97/05246 | 2/1997 |
| WO | WO 99/28480 | 6/1999 |
| WO | WO 01/21820 A1 | 3/2001 |
| WO | WO 01/22806 A | 4/2001 |
| WO | WO 03/095655 A2 | 11/2003 |
| WO | WO 2006/125297 A1 | 11/2006 |

OTHER PUBLICATIONS

Shen, Identification of a mitochondrial glycerol-3-phosphate dehydrogenase from Arabidopsis thaliana: evidence for a mitochondnal glycerol-3-phosphate shuttle in plants, FEBS Letters vol. 536, Issues 1-3, Feb. 11, 2003, pp. 92-96.*
Zou et al, Issued patents database, Accession No. 10/088,079-1, filed Sep. 22, 1999.*
NP_187648, Gen Pept database, Apr. 20, 2007.*
Blomberg et al. (Journal of Bacteriology, 171:1087-1092, 1989).*
He et al. (Journal of Plant Physiology, 164:214-220, 2007).*
PCT International Search Report, PCT/CA2006/000667, dated Aug. 4, 2006.
PCT International Preliminary Report on Patentability, PCT/CA2006/000667 dated Nov. 6, 2007, 6 pages.
PCT Written Opinion of the International Searching Authority, PCT/CA2006/000667, dated Jul. 11, 2006.
Lin et al., Abscisic acid regulation of heterophylly in Marsilea quadrifolia L.: effects of R-(−) and S-(+) isomers, Journal of Experimental Botany, Nov. 2005, pp. 2935-2948, vol. 56, No. 421.
Chiwocha et al., The etr1-2 mutation in Arabidopsis thaliana affects the abscisic acid, ausin, cytokinin and gibberellin metabolic pathways during maintenance of seed dormancy, moist-chilling and germination, The Plant Journal, 2005, pp. 35-48, vol. 42.
Clark et al., "Regulation of Phospholipid Biosynthesis in *Escherichia coli*: Cloning of the Structural Gene for the Biosynthetic sn-Glycerol-3-Phosphate Dehydrogenase," The Journal of Biological Chemistry, Jan. 25, 1980, pp. 714-717, vol. 255, No. 2.
Edgar et al., "Biosynthesis in *Escherichia coli* of sn-Glycerol 3-Phosphate, a Precursor of Phospholipid: Purification and Physical Characterization of Wild Type and Feedback-Resistant Forms of the Biosynthetic sn-Glycerol-3-Phosphate Dehydrogenase," The Journal of Biological Chemistry, Sep. 25, 1978, pp. 6348-6353, vol. 253, No. 18.
Gee et al., "Two Isoforms of Dihydroxyacetone Phosphate Reductase from the Chloroplasts of Dunaliella tertiolecta," Plant Physiol., 1993, pp. 243-249, vol. 103.
Hausmann et al., "Cloning of a cDNA Coding for a Glycerol-3-Phosphate Dehydrogenase from Cuphea lanceolata," Plant Lipid Metabolism, 1995, pp. 534-536.

(Continued)

*Primary Examiner*—Vinod Kumar
(74) *Attorney, Agent, or Firm*—TraskBritt

(57) ABSTRACT

The invention discloses methods for genetically transforming a plant so that it expresses a glycerol-3-phosphate dehydrogenase. The method raises levels glycerol-3-phosphate in comparison to the wild type, leading to increased stress tolerance, and altered fatty acid content in glycerolipids. The method also produces plants having improved phosphorus utilization.

14 Claims, 14 Drawing Sheets
(6 of 14 Drawing Sheet(s) Filed in Color)

OTHER PUBLICATIONS

Larsson et al., "A gene encoding sn-glycerol 3-phosphate dehydrogenase (NAD+) complements an osmosensitive mutant of Saccharomyces cerevisiae," Molecular Microbiology, 1993, pp. 1101-1111, vol. 10, No. 5.

Gee et al., Dihydroxyacetone Phosphate Reductase in Plants, Plant Physiol., 1988, pp. 98-103, vol. 86.

Gee et al., Differential Inhibition and Activation of Two Leaf Dihydroxyacetone Phosphate Reductases, Plant. Physiol., 1988, pp. 379-383, vol. 87.

Kirsch et al., Plant Dihydroxyacetone Phosphate Reductase, Plant Physiol., 1992, pp. 352-59, vol. 100.

Extended European Search Report, PCT/CA2006/000667, dated Dec. 23, 2008.

U.S. Appl. No. 12/448,061, filed Jun. 5, 2009, Genes Encoding a Novel Type of Lysophophatidylcholine Acyltransferases and Their Use to Increase Triacylglycerol Production and/or Modify Fatty Acid Composition.

* cited by examiner

Figure 1

```
  1 atgaaccaacgtaatgcttcaatgactgtgatcggtgccggctcg
    M  N  Q  R  N  A  S  M  T  V  I  G  A  G  S     15
 46 tacggcaccgctcttgccatcaccctggcaagaaatggccacgag
    Y  G  T  A  L  A  I  T  L  A  R  N  G  H  E     30
 91 gttgtcctctggggccatgaccctgaacatatcgcaacgcttgaa
    V  V  L  W  G  H  D  P  E  H  I  A  T  L  E     45
136 cgcgaccgctgtaacgccgcgtttctccccgatgtgccttttccc
    R  D  R  C  N  A  A  F  L  P  D  V  P  F  P     60
181 gatacgctccatcttgaaagcgatctcgccactgcgctggcagcc
    D  T  L  H  L  E  S  D  L  A  T  A  L  A  A     75
226 agccgtaatattctcgtcgtcgtacccagccatgtctttggtgaa
    S  R  N  I  L  V  V  V  P  S  H  V  F  G  E     90
271 gtgctgcgccagattaaaccactgatgcgtcctgatgcgcgtctg
    V  L  R  Q  I  K  P  L  M  R  P  D  A  R  L    105
316 gtgtgggcgaccaaagggctggaagcggaaaccggacgtctgtta
    V  W  A  T  K  G  L  E  A  E  T  G  R  L  L    120
361 caggacgtggcgcgtgaggccttaggcgatcaaattccgctggcg
    Q  D  V  A  R  E  A  L  G  D  Q  I  P  L  A    135
406 gttatctctggcccaacgtttgcgaaagaactggcggcaggttta
    V  I  S  G  P  T  F  A  K  E  L  A  A  G  L    150
451 ccgacagctatttcgctggcctcgaccgatcagacctttgccgat
    P  T  A  I  S  L  A  S  T  D  Q  T  F  A  D    165
496 gatctccagcagctgctgcactgcggcaaaagtttccgcgtttac
    D  L  Q  Q  L  L  H  C  G  K  S  F  R  V  Y    180
541 agcaatccggatttcattggcgtgcagcttggcggcgcggtgaaa
    S  N  P  D  F  I  G  V  Q  L  G  G  A  V  K    195
586 aacgttattgccattggtgcggggatgtccgacggtatcggtttt
    N  V  I  A  I  G  A  G  M  S  D  G  I  G  F    210
631 ggtgcgaatgcgcgtacggcgctgatcacccgtgggctggctgaa
    G  A  N  A  R  T  A  L  I  T  R  G  L  A  E    225
676 atgtcgcgtcttggtgcggcgctgggtgccgaccctgccacctttt
    M  S  R  L  G  A  A  L  G  A  D  P  A  T  F    240
721 atgggcatggcggggcttggcgatctggtgcttacctgtaccgaa*
    M  G  M  A  G  L  G  D  L  V  L  T  C  T  E    255
766 aaccagtcgcgtaaccgccgttttggcatgatgctcggtcagggc
    N  Q  S  R  N  R  R  F  G  M  M  L  G  Q  G    270
811 atggatgtacaaagcgcgcaggagaagattggtcaggtggtggaa
    M  D  V  Q  S  A  Q  E  K  I  G  Q  V  V  E    285
856 ggctaccgcaatacgaaagaagtccgcgaactggcgcatcgcttc
    G  Y  R  N  T  K  E  V  R  E  L  A  H  R  F    300
901 ggcgttgaaatgccaataaccgaggaaatttatcaagtattatat
    G  V  E  M  P  I  T  E  E  I  Y  Q  V  L  Y    315
946 tgcggaaaaaacgcgcgcgaggcagcattgactttactaggtcgt
    C  G  K  N  A  R  E  A  A  L  T  L  L  G  R    330
991 gcacgcaaggacgagcgcagcagccactaa 1020
    A  R  K  D  E  R  S  S  H  *                   339
```

METHODS OF PRODUCING AND GROWING PLANTS HAVING IMPROVED PHOSPHORUS UTILIZATION

CROSS-REFERENCE TO RELATED APPLICATIONS

This application is a continuation-in-part of U.S. patent application Ser. No. 10/088,079, filed Jul. 19, 2002, now U.S. Pat. No. 7,112,724, issued on Sep. 26, 2006, which is a national stage entry of and claims priority under 35 U.S.C. 0365(a) to PCT International Application PCT/CA00/01096 filed Sep. 21, 2000, corresponding to WO 01/21820, published in English on Mar. 29, 2001, which itself claims priority to U.S. Provisional Application 60/155,133, filed Sep. 22, 1999, each of the contents of which are incorporated herein by this reference.

TECHNICAL FIELD

The invention relates to biotechnology. More particularly, the invention relates to the field of plant genetic engineering. More specifically, the invention relates to methods of producing and growing transgenic plants having improved phosphorus utilization.

BACKGROUND

Phosphorus (P) is an essential nutrient for plant growth, development, and reproduction. After nitrogen, P is considered to be the second most important nutrient limiting agricultural production. Although the total amount of phosphorus in the soil may be high, it is often present in unavailable forms for plant uptake. For instance, Saskatchewan soils are inherently low in available P which ranges from 400 to 2000 lb/A in the top 6 inches of soil, but only an extremely small amount of the total P is available to the crop during a growing season. To reduce P deficiencies and ensure plant productivity, nearly 30 million tons of P fertilizers are applied to soils worldwide every year (e.g., P fertilizer is needed on about 85% of Saskatchewan cropland). Up to 80% of the P from the fertilizer is lost because it becomes immobile and unavailable for plant uptake because of adsorption, precipitation or conversion to organic forms. Moreover, in recent years increasing attention has been paid to the effect of excessive use of fertilizers, particularly P, in environmental pollution.

P helps plants store and use energy from photosynthesis to move nutrients into the plant and between cells, and produce sugars, starch and protein required for growth. In response to inorganic P limitations, some plants undergo physiological and developmental adaptations to scavenge limited phosphate from the environment, including decrease of their inorganic P consumption and mobilization of their inorganic P reserve. Phospholipids are the main form of cellular inorganic P reserve and their content markedly declines in plant during inorganic P starvation. In plants, glycerol-3-phosphate (G-3-P) is an obligated precursor for phospholipids synthesis, Further, G-3-P metabolism reflects perturbations of the general metabolic network.

The G-3-P synthesis enzyme, NAD+-dependent glycerol-3-phosphate dehydrogenase, is possibly a metabolic link between the cytosol and mitochondria that is necessary and essential for cellular redox control. Thus, G-3-P metabolism, particularly the activity of cytosolic G-3-P dehydrogenase is critical for many aspects of plant stress tolerance, including inorganic P limitation adaptation.

Glycerol-3-phosphate dehydrogenase (GPDH) (EC 1.1.1.8) is an essential enzyme for both prokaryotic and eukaryotic organisms. GPDH catalyses the reduction of dihydroxyacetone phosphate (DHAP) to glycerol-3-phosphate (G-3-P) using NADH as a reducing equivalent. Plant cells possess at least two isoforms of GPDH, one located in the plastids and the other in the cytosol.[1] The purification of the cytosolic GPDH from spinach has been reported.[2] The product of the reaction catalyzed by GPDH, G-3-P, is a precursor for the synthesis of all glycerol lipid species, including membrane and storage lipids. The biosynthetic role of this enzyme in bacteria was established in vivo by the isolation of glycerol and G-3-P auxotrophs of *E. coli* mutant strains deficient in its activity.[3] These mutants could not synthesize phospholipid in the absence of supplemental G-3-P.

There are no reports of plant mutants defective in GPDH activity.

In addition to being essential for lipid biosynthesis, GPDH is involved in several other important biological processes. Most notably, GPDH, through consuming NADH and regenerating $NAD^+$, plays an important role in maintaining cellular redox status. The $NAD^+$/NADH couple plays a vital role as a reservoir and carrier of reducing equivalents in cellular redox reactions. For catabolic reactions to proceed, the ratio $NAD^+$/NADH should be high. Under normal aerobic conditions, excessive NADH is channeled into mitochondria and consumed through respiration. Under anaerobic conditions, GPDH reactions serve as a redox valve to dispose of extra-reducing power. In this way, the cellular NAD+/NADH ratio can be maintained at a level allowing catabolic processes to proceed. The expression of the GPDH gene is subject to redox control and induced by anoxic conditions in *Saccaromyces cerevisae*. Deletion of the GPD2 gene (one of the two isoforms of GPDH) results in defective growth under anaerobic conditions.[4]

GPDH has also been shown to play an important role in adaptation to osmotic stress in *S. cerevisae*. GPDH exerts its role in osmotic and salinity stress response through its function in glycerol synthesis. Glycerol is a known osmo-protectant. It is produced from G-3-P through dephosphorylation by a specific glycerol 3-phosphatase. To respond to a high external osmotic environment, yeast cells accumulate glycerol to compensate for differences between extracellular and intracellular water potentials.[5] The expression of the GPDH gene, GPD1, has been demonstrated to be osmoresponsive.[6] A strain of *S. cerevisae* in which the GPD1 gene has been deleted is hypersensitive to NaCl.[7] Accumulation of glycerol as an osmoregulatory solute has been reported in some halophilic green algae including *Dunaliella, Zooxanthellae, Asteromonas* and *Chlamydonas reinhardtii*.[8]

The sequence of a cDNA encoding GPDH activity has been reported for the plant *Cuphea lanceolata*.[9] The encoded protein was tentatively assigned as a cytosolic isoform.

To date, there has been no report on the genetic manipulation of plant GPDH.

SUMMARY OF THE INVENTION

The inventors have surprisingly found that transgenic plants capable of overexpressing a glycerol-3-phosphate dehydrogenase grow well in phosphorus (P) limiting conditions. Thus, the development of the transgenic plants described herein represents a way to achieve a more sustainable agriculture that could help satisfy the growing world demand for food. Furthermore, the transgenic plants with an increased P acquisition capacity that are more efficient in the use of P should be of great importance for subsistence farmers, who cannot afford commercial P fertilizer and help reduce costs for commercial farmers.

In one embodiment, an *Escherichia coli* gene, gpsA that encodes a G-3-P dehydrogenase under the transcription control of a strong constitutive promoter, e.g., the cauliflower mosaic virus 35S promoter, is used to generate transgenic plants in *Arabidopsis* and *Brassica napus* to produce transgenic plants with G3P levels several fold higher than that of wild type plants. In the transgenic plants, the glycerolipid biosynthesis metabolic flux between the prokaryotic and eukaryotic glycerolipid pathways adjusted in responding to G-3-P changes. In comparison to wild type plants, higher proportion of cellular membrane lipid molecules was derived from the plastidic prokaryotic glycerolipid pathway, which produces mainly monogalactosyldiacylglycerol (MGDG) and digalactosyldiacylglycerol (DGDG). Consequently, the ratio of phospholipids versus non-phospholipids in the transgenic plants was reduced. Thus, these transgenic plants were able to maintain cellular activity while using less P for membrane lipid biosynthesis. The results show that when compared to the controls, the transgenic plants (*Arabidopsis* and canola) yield more leaf and seeds biomass accompanied by higher chlorophyll content were high, lower anthocynines and starch when grown under P-limiting conditions. These results indicated that the transgenic plants are more resilient to P-limitation.

In one embodiment, a process for growing a transgenic plant, plant seed, or progeny thereof includes planting a transgenic plant, plant seed or progeny thereof having means for encoding a glycerol-3-phosphate dehydrogenase incorporated in the genome. The transgenic plant, plant seed or progeny thereof to maturity is grown to maturity and seed from the mature transgenic plant, plant seed or progeny thereof is harvested.

As used herein, the phrase "plant, plant seed or progeny thereof" will be used to refer to a plant or its progeny or seeds. For instance, "plant, plant seed or progeny thereof" will refer to the T1, T2 and T3 generation of a plant as well as to plants produced with asexual reproduction methods.

In a further embodiment, a transgenic canola plant, seed or progeny thereof comprises a genome having means for encoding a glycerol-3-phosphate dehydrogenase integrated in the genome. The means for encoding the glycerol-3-phosphate dehydrogenase is operatively linked to a promoter.

In an additional embodiment, a system for producing a plant, plant seed or progeny thereof includes soil having a reduced phosphorus content and a transgenic plant, plant seed or progeny thereof having a gene encoding a glycerol-3-phosphate dehydrogenase integrated in the genome. The transgenic plant, plant seed or progeny thereof is capable of growing in the soil having the reduced phosphorus content for about 60 days or for the growing season (or time to produce seed) of the plant.

In yet a further embodiment, a method for reducing an amount of phosphorus required to grow a crop plant includes obtaining a transgenic crop plant, plant seed or progeny thereof capable of growing in soil having a reduced phosphorus content for at least 60 days or the time to produce the crop, and planting the transgenic crop plant, plant seed or progeny in soil.

As used herein, the phrase "means for encoding a glycerol-3-phosphate dehydrogenase" will be used to refer to a gene encoding for a gpsA gene. In one embodiment, the gpsA gene is of prokaryotic origin. In another embodiment, the gpsA gene is of bacterial origin. Exemplary embodiments of gpsA genes include, but are not limited to, those originating from *E. coli* (SEQ ID NO: 1), *Shigella flexneri* (SEQ ID NO: 7), *Salmonella typhimurium* (SEQ ID NO: 9), *Salmonella enterica* (SEQ ID NO: 11), *Yersinia pestis* (SEQ ID NO: 13), *Yersinia pseudotuberculosis* (SEQ ID NO: 15), *Serratia marcescens* (SEQ ID NO: 17), *Photorhabdus luminescens* (SEQ ID NO: 19), *Erwinia carotovora* (SEQ ID NO: 21) or conservative substitutions thereof. The means for encoding a glycerol-3-phosphate dehydrogenase also includes variants or mutants of the exemplary gpsA genes that encode proteins having or possessing the same function as the glycerol-3-phosphate dehyrogenase encoded by the wild-type or mutant gpsA gene. For instance, silent mutations and conservative substitutions in genes are known to exist and, yet, encode proteins having the same function of the wild-type gene. In another embodiment, the means for encoding a glycerol-3-phosphate dehydrogenase comprises a nucleotide sequence encoding a glycerol-3-phosphate dehydrogenase protein having an amino acid sequence origating from *E. coli* (SEQ ID NO: 2), *Shigella flexneri* (SEQ ID NO: 8), *Salmonella typhimurium* (SEQ ID NO: 10), *Salmonella enterica* (SEQ ID NO: 12), *Yersinia pestis* (SEQ ID NO: 14), *Yersinia pseudotuberculosis* (SEQ ID NO: 16), *Serratia marcescens* (SEQ ID NO: 18), *Photorhabdus luminescens* (SEQ ID NO: 20), *Erwinia carotovora* (SEQ ID NO: 22) or conservative substitutions thereof.

In another embodiment, a method of producing a crop with less P is disclosed. The method includes planting a transgenic seed that is able to overexpress a glycerol-3-phosphate dehydrogenase. In one embodiment, the transgenic seed includes a heterolgous gene encoding a glycerol-3-phosphate dehydrogenase protein that is of a prokaryotic, bacterial, eukaryotic, yeast, or plant origin, wherein the heterolgous gene encoding the glycerol-3-phosphate dehydrogenase protein provides the transgenic plant with the ability to grown in the soil with the reduced P content. The transgenic seed is able to grow in soil having a reduced amount of P and, yet, grow in substantially the same manner as wild type plants in soil having been fertilized with P or soil having a suitable amount of P. As used herein, the term "reduced phosphorus content" will be used to refer to soils that are in need of exogenous P or Pi to support the growth of a crop or have a P content of less than about 20 parts per million (ppm).

In yet an additional embodiment, the transgenic seed capable of overexpressing a glycerol-3-phosphate dehydrogenase and, thus, growing in soil having a reduced amount of P is marketed and sold. The transgenic seed is sold in containers associated with indicia that direct a user of the transgenic seed of the amount of P required in the soil to support the growth of the transgenic seed. In this manner, the user of the transgenic seed is able to reduce the amount of P fertilizer that is applied to the soil or even avoid having to place P fertilizer on the soil, thus, reducing the operating costs for the user of the transgenic seed.

In one embodiment, it is shown that transgenic over-expression of a glycerol-3-phosphate dehydrogenase gene, such as gpsA, increases the amount of G-3-P, decreases the content of phospholipids, and consequently enhances plant tolerance to low Pi availability. Crops species, such as maize, wheat, bean, rice, vegetables, and tree species that are all susceptible to low P availability, are also targets (crops) for the introduction of gene involved in G-3-P and phospholipids metabolism.

In one embodiment, a method for expressing a heterologous glycerol-3-phosphate dehydrogenase in a plant is disclosed.

In another embodiment, a plant expressing a heterologous glycerol-3-phosphate dehydrogenase is described, wherein the heterologous glycerol-3-phosphate dehydrogenase is subject to less feedback inhibition than wild type glycerol-3-phosphate dehydrogenase.

In yet an additional embodiment, a genetically altered plant exhibiting altered fatty acid content in its glycerolipids is disclosed.

In one embodiment, a genetically altered plant exhibiting enhanced tolerance to osmotic stress in comparison to the wild type plant is described.

In yet a further embodiment, a genetically altered plant exhibiting increased stress tolerance in comparison to the wild type plant is described.

In an additional embodiment, the invention discloses a method for expressing a heterologous glycerol-3-phosphate dehydrogenase that is less sensitive to feedback inhibition than wild type glycerol-3-phosphate dehydrogenase in a plant, the method comprising providing a vector comprising a DNA sequence encoding a glycerol-3-phosphate dehydrogenase that is less sensitive to feedback inhibition than wild type glycerol-3-phosphate dehydrogenase; and transforming the plant with the vector.

In another embodiment, the invention discloses a plant expressing a heterologous glycerol-3-phosphate dehydrogenase that is less sensitive to feedback inhibition than wild type glycerol-3-phosphate dehydrogenase.

In one embodiment, the invention discloses a method for producing a genetically-altered plant having altered fatty acid content in its glycerolipids, the method comprising providing a vector comprising a DNA sequence encoding a glycerol-3-phosphate dehydrogenase that is less sensitive to feedback inhibition than wild type glycerol-3-phosphate dehydrogenase; and transforming the plant with the vector.

In a further embodiment, the invention discloses a method for producing a plant having increased glycerol and/or glycerol-3-phosphate levels, the method comprising providing a vector comprising a DNA sequence encoding a glycerol-3-phosphate dehydrogenase that is less sensitive to feedback inhibition than wild type glycerol-3-phosphate dehydrogenase; and transforming the plant with the vector.

In an additional embodiment, the invention discloses a method for producing a genetically-altered plant having increased stress tolerance relative to the wild type, the method comprising providing a vector comprising a DNA sequence encoding a glycerol-3-phosphate dehydrogenase that is less sensitive to feedback inhibition than wild type glycerol-3-phosphate dehydrogenase; and transforming the plant with the vector.

In a further embodiment, the invention discloses a method for producing a genetically-altered plant having increased osmotic stress tolerance relative to the wild type, the method comprising providing a vector comprising a DNA sequence encoding a glycerol-3-phosphate dehydrogenase that is less sensitive to feedback inhibition than wild type glycerol-3-phosphate dehydrogenase; and transforming the plant with the vector.

In yet an additional embodiment, the invention discloses a method for increasing the cellular glycerol-3-phosphate dehydrogenase activity in a plant, the method comprising providing a vector comprising a DNA sequence encoding a glycerol-3-phosphate dehydrogenase that is less sensitive to feedback inhibition than wild type glycerol-3-phosphate dehydrogenase; and transforming the plant with the vector.

In yet another embodiment, the invention discloses a vector for genetically transforming a plant, wherein the vector comprises a DNA encoding a protein having glycerol-3-phosphate dehydrogenase activity, and the plant, after transforming, exhibits enhanced production of glycerol and/or glycerol-3-phosphate.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 shows the nucleotide sequence and the deduced amino acid sequence of the *E. coli* gpsA2$^{FR}$ gene. The point mutation is highlighted and denoted by '*';

FIG. 17B shows watering with non-Pi solution (80 ml/pot) every day. FIG. 17A depicts the canola seedlings grown for 68 days in sand, and FIG. 17B illustrates canola grown for 100 days in sand.

BEST MODE OF THE INVENTION

Figure 2:
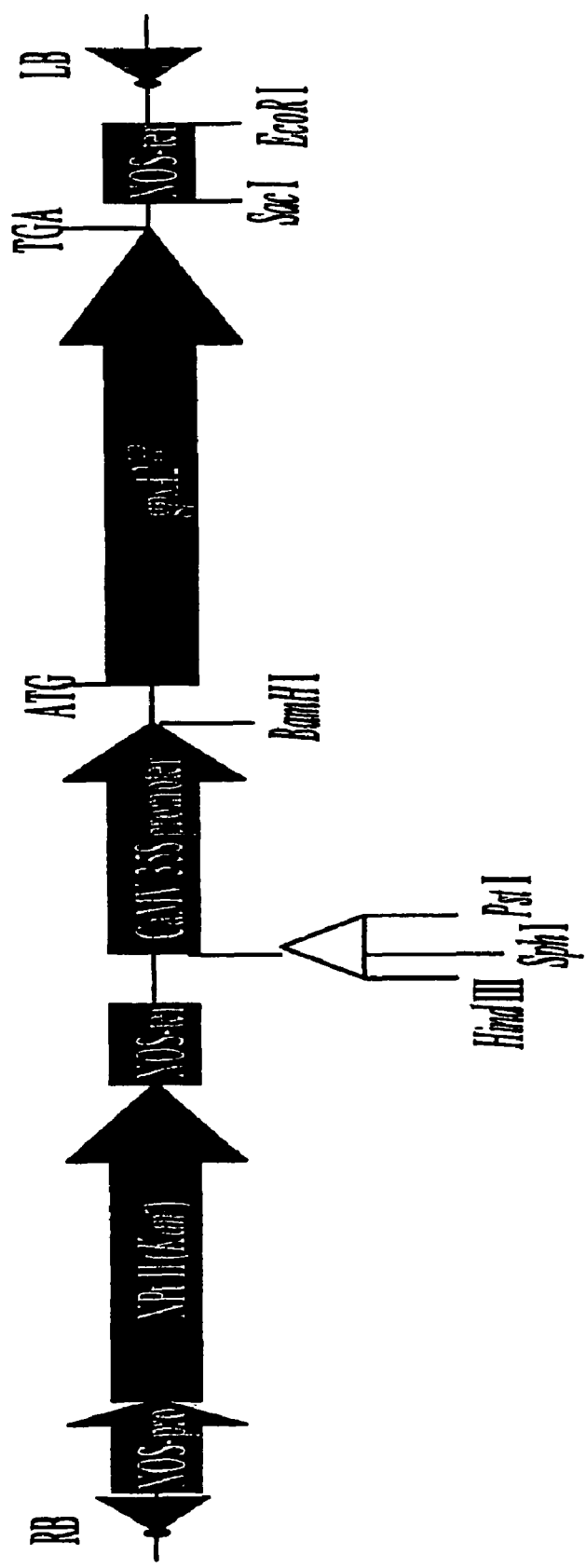
FIG. 2 shows a diagram of the gpsA2$^{FR}$ plant transformation vector, pGPSA-VI, not drawn to scale.
Figure 3:
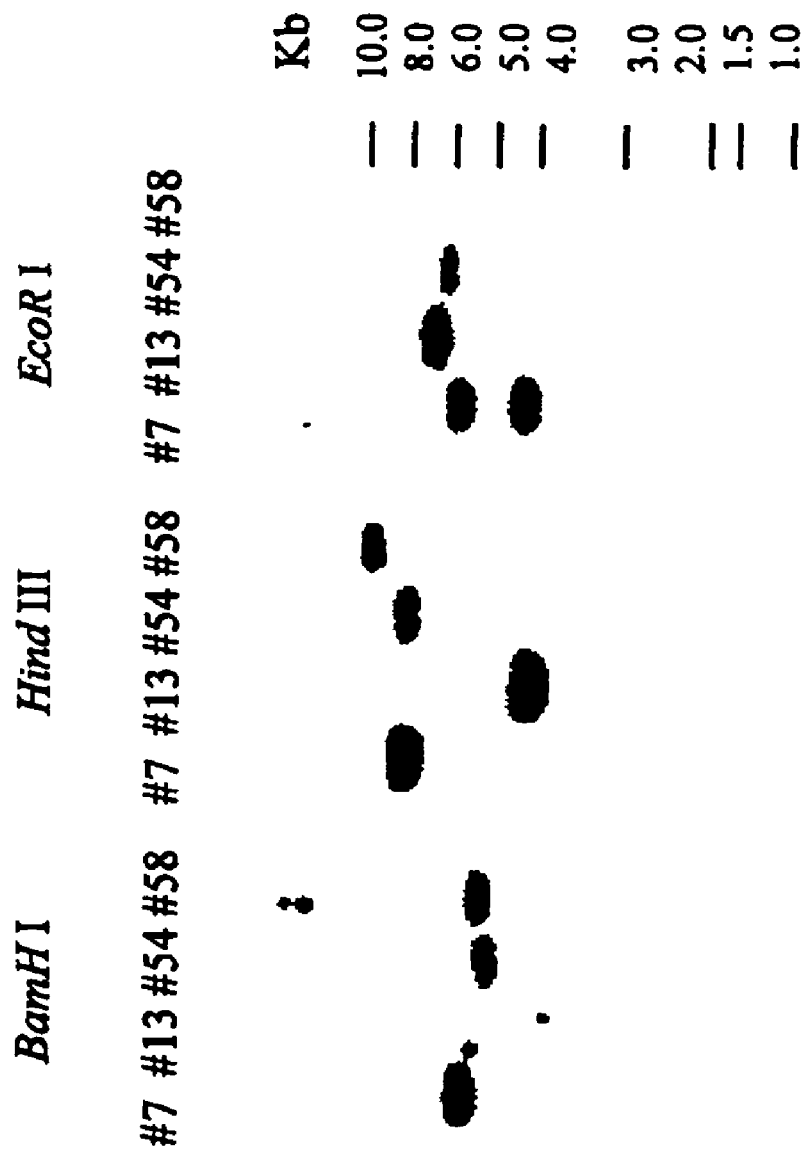
FIG. 3 shows a southern blot analysis with respect to the gpsA2$^{FR}$ gene among the selected independent *A. thaliana* transgenic lines.

The inventors' discoveries of utility of transgenic plants have continued. For instance, the inventors discovered that transgenic *Arabidopsis* plants were able to have increased osmotic stress tolerance and altered fatty acid content in glycerolipids. (See, PCT International Publication WO 01/21820 A1, published Mar. 29, 2001, the contents of the entirety of which is incorporated by this reference).

Due to its role in lipid biosynthesis, as well as in the stress responses, an increased GPDH activity in plants is desirable. Transgenic approaches to over express either a plant or a non-plant GPDH gene in a plant can, in principle, be expected to increase GPDH activity. However, there are several advantages inherent in inserting a non-plant gene into a plant genome. It is well established that introducing the same plant gene back to its originating species, even under sense-orientation, can result in a decrease of the over all enzyme activity due to co-suppression. Genes of different origin (heterologous), especially those from evolutionarily distantly related species, can be expected to be free of this impediment. More importantly, proteins of identical enzymatic function are often regulated through different schemes in different species. A heterologous enzyme may potentially be free of controlling factors that inhibit the endogenous enzyme.

The heterologous enzyme that is expressed in the plant in the method of the invention may be any glycerol-3-phosphate dehydrogenase that exhibits decreased inhibition of glycerol-3-phosphate production in the plant. Such enzymes are called feed-back defective. In one embodiment, the heterologous enzyme is a glycerol-3-phosphate dehydrogenase having a single amino acid mutation. The mutation should not greatly decrease glycerol-3-phosphate dehydrogenase activity, but should decrease inhibition of the enzyme by glycerol-3-phosphate. One allele of the *E. coli* gpsA gene, gpsA2$^{FR}$, has been reported to encode an altered version of the GPDH protein, defective in feedback inhibition.[10] In a preferred embodiment, the method of the invention uses a vector comprising the gene gpsA2$^{FR}$. The inventors identified a point mutation in the gspA2$^{FR}$ sequence: replacement of A by C in the third nucleotide of codon 255 in gpsA. The mutation results in substitution of Glu$^{255}$ (GAA) for Asp$^{255}$ (GAC) in the encoded protein. The sequences of the g-psA2$^{FR}$ gene and the deduced amino acid sequence of the gene are shown in FIG. 1. The gene sequence is listed in SEQ ID NO: 1, and the encoded protein is listed in SEQ ID NO: 2. In other embodiments, the gene sequences are any one of SEQ ID NO: 1, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21 and conservative mutants thereof.

The vector may be any vector that is suitable for transforming the plant species used. Examples of suitable vectors include pHS737, pHS738, pRD400[11]; pBin19[12]; and pCGN3223.[13]

GPDH is common to the biosynthetic pathway of all plants. The method of the invention can, therefore, be used with any plant. In one embodiment, the inventors used the model plant species *A. thaliana*. As a result of the ease with which this plant lends itself to work in both classical and molecular genetics, *Arabidopsis* has come to be widely used as a model organism in plant molecular genetics, development, physiology and biochemistry.[14,15,16] This dicotyledonous plant is also closely related to *Brassica* crop genus and it is increasingly apparent that information concerning the genetic control of basic biological processes in *Arabidopsis* will be transferable to other species.[17]

Indeed, numerous examples exist where studies of the molecular biology and biochemistry of a particular metabolic pathway or developmental process and the possibility of genetically engineering a plant to bring about changes to said metabolic pathway or process, has first been tested in the model plant *Arabidopsis*, and then shown to yield similar phenotypes in other plants, particularly crop plants.

Expressing a heterologous GPDH in a plant, according to the method of the invention, leads to altered fatty acid content in the triacylglycerols of the plant. It is often desirable to alter the fatty acid content of glycerolipids to achieve certain desired characteristics in oil seeds. For example, for oils destined for human consumption, it may be desired to increase unsaturated fatty acid content. For other uses, it may be desirable to increase the saturated fatty acid content. The inventors have found that plant transformants over-expressing the gpsA2$^{FR}$ gene produce glycerolipids having an increased proportion of 16 carbon fatty acids and a concomitant decrease of 18 carbon fatty acids.

Due to the relationship of GPDH to glycerolipid synthesis, the method of the invention is particularly suited for use with oil seed bearing plants. The term "oil seed bearing plant" is meant to encompass any plant or crop from which the oil may be isolated in marketable quantity. Some plants or crops having glycerolipids with particularly interesting fatty acid composition are grown for the production of glycerolipids, even though the lipid content is low (e.g., less than 1 wt %). The method of the invention may be used in such plants to modify the fatty acid content of the glycerolipid. Preferred plants or crops are those having a seed lipid content of at least 1 wt %. Some illustrative examples of oil seed crops are as follows (trivial names are given in parentheses):

*Borago officinalis* (borage); *Brassica* species, for example mustards, canola, rape, *B. campestris, B. napus, B. rapa; Cannabis sativa* (hemp, widely used as a vegetable oil in Asia); *Carthamus tinctorius* (safflower); *Cocos nucifera* (coconut); *Crambe abyssinica* (crambe); *Cuphea* species (*Cuphea* produce medium chain fatty acids of industrial interest); *Elaeis guinensis* (African oil palm); *Elaeis oleifera* (American oil palm); *Glycine max* (soybean); *Gossypium hiristum* (cotton—American); *Gossypium barbadense* (cotton—Egyptian); *Gossypium herbaceum* (cotton—Asiatic); *Helianthus annus* (sunflower); *Linum usitatissimum* (linseed or flax); *Oenethera biennis* (Evening primrose); *Olea europea* (olive); *Oryza sativa* (rice); *Ricinus communis* (castor); *Sesamum indicum* (sesame); *Soja max* (soybean—note, glycine max is the major species); *Triticum* species (wheat); and *Zea maize* (corn).

GPDH consumes NADH, and, therefore, plays an important role in maintaining a healthy cellular redox balance. Stress conditions often result in perturbation of plant metabolism, and particularly, redox status. Stress conditions include such things as dryness, excessive humidity, excessive heat, excessive cold, excessive sunlight, and physical damage to the plant. Such agents can lead to higher than normal levels of NADH. Excessive NADH can generate high concentrations of reactive oxygen species (ROS) that are hazardous to proteins and nucleic acids, and may even lead to cell death. An increased GPDH activity, as induced by the method of the invention, improves the capacity of plants to maintain cellular redox balance, thereby leading to an enhanced tolerance to stress.

Another type of stress suffered by plants is osmotic stress. This results when the plant is forced to grow in an environment in which the external water supply has an unusually high concentration of solute. The most usual solutes that are encountered include salts (particularly NaCl), however, in polluted areas, other solutes might be encountered. The method of the invention leads to increased levels of glycerol and/or gycerol-3-phosphate in the tissues of the transformed plant. Glycerol acts as an osmo-protectant, allowing the transformed plant to grow in conditions that would normally not support it.

A heterologous gene encoding GPDH activity can be introduced into genome of plants and expressed using conventional genetic engineering techniques. The most developed methodology for inserting genes into plant genomes is *Agrobacterium tumefaciens* mediated transformation. Other techniques known in the art of introducing DNA into plants include electroporation, chemically-mediated DNA uptake, and the use of microprojectiles.

The invention will be described in more detail with reference to the following examples. The examples serve only to illustrate the invention.

EXAMPLES

Example I

Molecular Biological Techniques

For a general description of some of the techniques used, see Ausebel et al. *Current protocols in Molecular Biology*, Vols 1, 2, 3, (1995) New York: Wiley, incorporated herein by reference.

Example II

Identification of the Point Mutation of the gpsA2$^{FR}$ Gene from *E. coli* Strain BB26R In order to investigate the structure of the gpsA2$^{FR}$ gene, the inventors synthesized two primers, TTAGTGGCTGCT-GCGCTC (GPSA3, SEQ ID NO: 3) and AACAATGAAC-CAACGTAA (GPSA5, SEQ ID NO: 4), complementary to the sequences corresponding to the 3' and 5' end of the gpsA gene, respectively. PCR amplifications were performed with template DNA isolated from wild type *E. coli* K12 and from strain BB26R, respectively. The BB26R strain harboring the gpsA2$^{FR}$ allele can be obtained according to Cronan et al. The PCR products were purified with QIAquick™ PCR purification Kit (Qiagen™) and fully sequenced. The sequences of gpsA (wild type) and gpsA2$^{FR}$ (mutant) were compared through sequence alignment using the computer program DNAstar™.

Example III

Construction of a Plant Transformation vector for gpsA$^{FR}$

Primers GAGAGCTCTTAGTGGCTGCTGCGCTC (GPSA31, SEQ ID NO: 5) and GAAGAAGGATCCAA-CAATGAACCAACGTAA (GPSA51, SEQ ID NO: 6) were designed according to the sequence of gpsA2$^{FR}$. At the 5' end of GPSA31, a SacI restriction site was added, while a BamHI restriction site was added at the 5' end of GPSA5. The primers were used to perform PCR amplification of the gpsA2$^{FR}$ sequence. The PCR products were purified with QIAquick™ PCR purification Kit (Qiagen) and digested with SacI/BamHI. The SacI/BamHI digested gpsA2$^{FR}$ DNA fragment was subsequently inserted into the *Agrobacterium* binary vector pBI121 (Clontech) to replace the SacI/BamHI region covering the GUS gene. The resultant plant transformation vector is designated as pGPSA-VI (deposited Aug. 31, 2000, at the American Type Culture Collection, 10801 University Blvd., Manassas, Va. 20110-2209, accession no. PTA-2433). The gpsA2FR gene expression cassette in pGPSA-VI contains the gpsA2$^{FR}$-encoding region driven by the constitutive 35S promoter. Its 3' end is flanked by the NOS terminator. The junction region between the 35S promoter and the gpsA2$^{FR}$ encoding sequence in pGPSA-VI was confirmed through sequencing. The gpsA$_2^{FR}$ protein will thus be expressed in all plant tissues including vegetative and reproductive (seed) tissues once the gene expression cassette is incorporated into the plant genome.

Example IV

Plant Growth Conditions

*A. thaliana* was chosen as the plant host to test the effect of the gpsa2$^{FR}$ gene since it is widely recognized as a laboratory model plant for genetic and biochemical studies. Moreover, *A. thaliana* in many aspects resembles canola such as, for example, *Brassica napus*, and is considered an oilseed plant. Genetic manipulations that are successful with *A. thaliana* can be applied to other species.[18] All *A. thaliana* control and transgenic plants were grown at the same time, in controlled growth chambers, under 16 hr fluorescent illumination (150-200 µE/m/sec), 8 hr dark at 22° C., as described previously.[19]

Example V

Plant Transformation

Plasmid pGPSA-VI was introduced into *A. tumefaciens* strain GV3101 bearing helper nopaline plasmid pMP90, via electroporation. Wild type *A. thaliana* plants of ecotype Columbia were grown in soil. Plants one week after bolting were vacuum-infiltrated overnight with a suspension of *A. tumefaciens* strain GV3101 harboring pGPSA-VI[20].

After infiltration, plants were grown to set seeds (T1). Dry seeds (T1) were harvested in bulk and screened on selective medium with 50 mg/L kanamycin. After two to three weeks on selective medium, kanamycin resistant seedlings (T1) which appeared as green were transformed to soil to allow growing to maturity. Seeds (T2) from the T1 plants were harvested and germinated on kanamycin plates to test segregation ratios. A typical single gene insertion event would give rise to a kanamycin resistant/sensitive ratio of 3:1. To further confirm the integration of the gpsA2$^{FR}$ gene, DNA was isolated from selected transgenic lines to perform Southern blot analysis with probes prepared with gpsA2$^{FR}$ DNA. Total RNA was also isolated for Northern analysis to confirm the expression of the gpsA2$^{FR}$ gene. Subsequent generations of plants that retain the transgenic traits of the transgenic plant are referred to as plants, plant seeds or progeny thereof, e.g., T1, T2 and T3 generations of plants.

Example VI

Fatty Acid Profile Analysis

Lipids were isolated from developing leaves as described by Katavic et al.,[21] and the fatty acid compositions were analyzed by Gas Chromatography.

Example VII

Analysis of Plant Tolerance Towards Salinity Stress

The salt tolerance of *A. thaliana* ecotype Columbia (wild-type) plants and plants over-expressing the gpsA2$^{FR}$ gene was measured using a protocol reported by Apse et al.[22] Pots of wild-type plants and each of the four transgenic lines (designated as #7, #13, #54 and #58) over-expressing gpsA2$^{FR}$ gene were divided into five groups (labeled A through E). The plants were planted in 4' pots with each pot containing 4 plants. The plants were grown for two weeks with nutrients only (22 g of 20:20:20 plant nutrient (Plant Products Co. Ltd., Canada) in 80 liters of water) solutions to ensure even growth of all plants. Afterwards, every alternate day over a 16-day watering regime, 25 ml of a diluted nutrient solution was applied. The control (A) group received the nutrient-only solution with no NaCl supplementation. The remaining groups were watered with nutrient solution supplemented with NaCl. The concentrations of NaCl supplementation were increased stepwise by 50 mM every 4 days for each group, to the indicated maximum: (A) 0 mM NaCl, (B) 50 mM NaCl, (C) 100 mM NaCl, (D) 150 mM NaCl, and (E) 200 mM NaCl. The plants were monitored for their phenotype, flowering time, etc.

Seed germination assays were performed with surface sterilized *Arabidopsis* seeds of wild type and selected T3 transgenic lines sown in Petri dishes containing 20 ml half strength MS medium,[23] supplemented with B5 vitamins and 2% sucrose. For the salt stress germination assay, various concentrations of NaCl were added. Cultures were grown at 22° C. under fluorescent light, 16 h light and 8 h dark. Seed germination was recorded after a period of 10 days. The emergence of radicle and cotyledons was considered as evidence of germination.

Example VIII

The gpsA2$^{FR}$ Gene Has a Point Mutation That Alters One Amino Acid Residue in the GPDH Protein (gpsA2$^{FR}$)

The biosynthesis of G-3-P in *E. coli* was initially investigated by Kito and Pizer.[24] The gpsA locus located at minute 71 of the *E. coli* genetic map was determined to be the structural gene for the biosynthetic glycerol-3-phosphate dehydrogenase by Cronan and Bell.[25] The nucleotide sequence and the deduced amino acid sequence of the *E. coli* gpsA gene was reported previously.[26] Biochemical studies on phospholipid biosynthesis mutants indicated that the cellular level of G-3-P must be tightly regulated Bell (1974), *J. Bacteriol*. 117, 1065-1076. The *E. coli* mutant, plsB, possesses a glycerol-P acyltransferase with an apparent $K_m$ for G-3-P over 10 times higher than normal. Subsequently, revertants of the plsB mutant, BB26R, were identified.[27] The glycerol-3-phosphate dehydrogenase activities of these revertants were about 20-fold less sensitive to feedback inhibition by G-3-P. These feedback resistant gpsA alleles were named gpsA2$^{FR}$. The molecular mechanism behind the gpsA2$^{FR}$ protein was unknown. The gpsA2$^{FR}$ gene was cloned from strain BB26R and its nucleotide sequence was determined. Sequence analysis indicated that gpsA2FR differs from gpsA at only one nucleotide base. The point mutation, a replacement of A from C at the third nucleotide of codon 255 in gpsA (FIG. 1) was founded in the gpsA2$^{FR}$ gene. This point mutation resulted in a change of Glu$^{25}$ (GAA) from Asp$^{255}$ (GAC) in the glycerol-3-phosphate dehydrogenase enzyme protein.

It has now been shown that the gpsA2$^{FR}$ gene harbors a point mutation in comparison to the wild type gpsA gene. The inventors have demonstrated that the point mutation is the reason why the GPDH enzyme is 20 time less sensitive to G-3-P feedback inhibition than the wild type. As a result, the cellular G-3-P could reach a level higher than a wild type gpsA could generate.

Example IX

Figure 4:
FIG. 4 shows a northern blot analysis of gpsA2$^{FR}$ gene expression in the *A. thaliana* transgenic lines.

Introduction of the gpsA2$^{FR}$ Gene Into Plant Genomes Does Not Affect Plant Development A large number of gpsA2$^{FR}$ transgenic plants were generated. These transgenic plants (T1) were initially screened for kanamycin resistance in kanamycin supplemented ½ MS medium. All T1 transgenic plants under our growing conditions appeared indistinguishable from wild type *A. thaliana* control, and developed at the same pace as that of the wild type plants when transferred into soil. The fertility and the seed yield were also not affected by the transgene. It, thus, proved that the integration of the gpsA2$^{FR}$ gene did not have any adversary effect on plant growth and reproduction. The segregation ratios of the (T2) seeds from the T1 plants with regard to kanamycin resistance were determined. Transgenic lines #7, #13, #54, #58 were selected for further study since segregation analysis indicated that these lines were single-insertion transgenic lines. To further verify the incorporation of gpsA$^{FR}$ gene into plant genome, genomic DNA was isolated from T3 plant seedlings of lines #7, #13, #54, #58, respectively. Southern analysis of genomic DNA digested with three different restriction enzymes showed that these lines contain a single copy of the gpsA2$^{FR}$ gene, and the transgene is inherently stable (FIG. 4). Northern analysis with RNA extracted from these lines confirmed that the gpsA2$^{FR}$ gene is expressed at a high level in these transgenic lines. Therefore, the introduction and expression of the gpsA2$^{FR}$ gene into higher plants was accomplished.

Example X

*A. thaliana* gpsA2$^{FR}$ Transformants have Altered Fatty Acid Profiles

Figure 5:
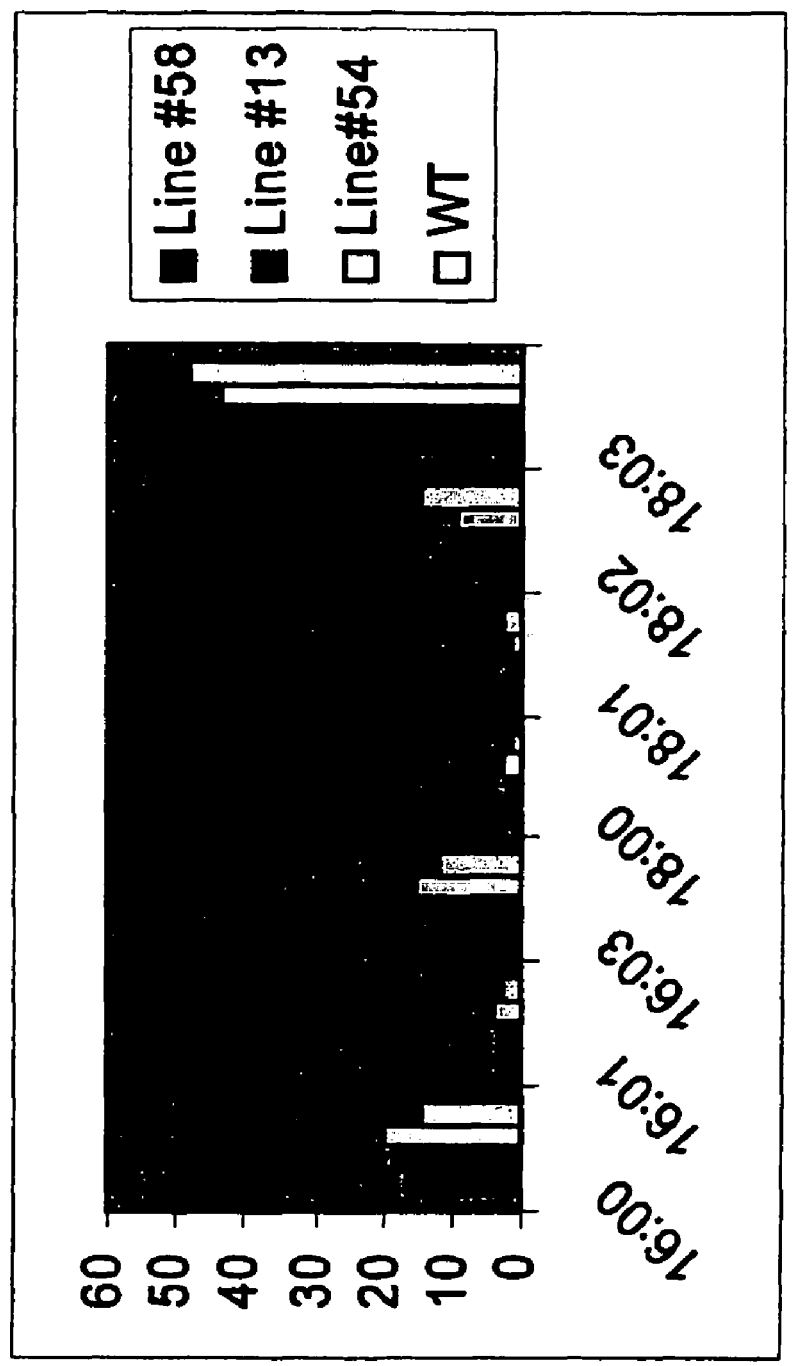
FIG. 5 shows the leaf fatty acid profiles of the selected gpsA2$^{FR}$ transgenic *A. thaliana* lines.

Total lipids were extracted from leaf tissues of transgenic plants as well as wild type control, and the fatty acid compositions were analyzed using Gas Chromatography. In order to minimize any difference that might exist during plant development, care was taken to ensure all plant leaves collected were at the same developmental stage. Reproducible results were obtained with leaves collected from several wild type plants, confirming that there were no significant differences with regard to fatty acid profiles among wild type plants. Data from leaves of the *A. thaliana* transgenic plants, however, indicated that the gpsA2$^{FR}$ gene product affects fatty acid composition. As shown in FIG. 5, gpsA2$^{FR}$ transgenic plants consistently showed elevated levels of 16 carbon fatty acids, and proportionately decreased level of 18 carbon fatty acid. Specifically, the transgenic plants showed about a 2-5% increase of 16:0, and about a 1.5-3.5% increase of 16:3 fatty acids. Concomitantly, the decrease on 18:2 and 18:3 fatty acids is at a 2-5% range (FIG. 5). Differences between the transgenic plants and the controls are also apparent if the ratios of the sum of 16-carbon (16C) fatty acid versus the sum of 18-carbon (18C) fatty acids are compared. For example, under the growing conditions described, transgenic line #58, line #13 and line #54 had 16C/18C ratios of 0.53, 0.6 and 0.68, respectively, while the ratio in control plants was 0.43. This phenotype is most likely a direct result of an increased supply of G-3-P generated by the high GPDH activity in the transgenic plants. It is consistent with previous report by Gardiner et al., in which an increased ratio of 16C/18C fatty acids was observed among newly synthesized fatty acids when elevated amounts of G-3-P were fed to isolated plastids.[28]

Example XI

The gpsA2$^{FR}$ Gene Improved Plant Stress Tolerance

As stated previously, GPDH consumes NADH and regenerates NAD$^+$. Lowering cellular (NADH) has beneficial effects on mitochondrial respiration and energy charge. GPDH participates in the control of cellular redox status, and possibly reduces the concentration of potentially damaging reactive oxygen species. Plant cells are known to go through an oxidative burst under stress conditions, often leading to cell death.

The present study revealed that the gpsA2$^{FR}$ transgenic plants possessed enhanced salinity tolerance.

Figure 6:
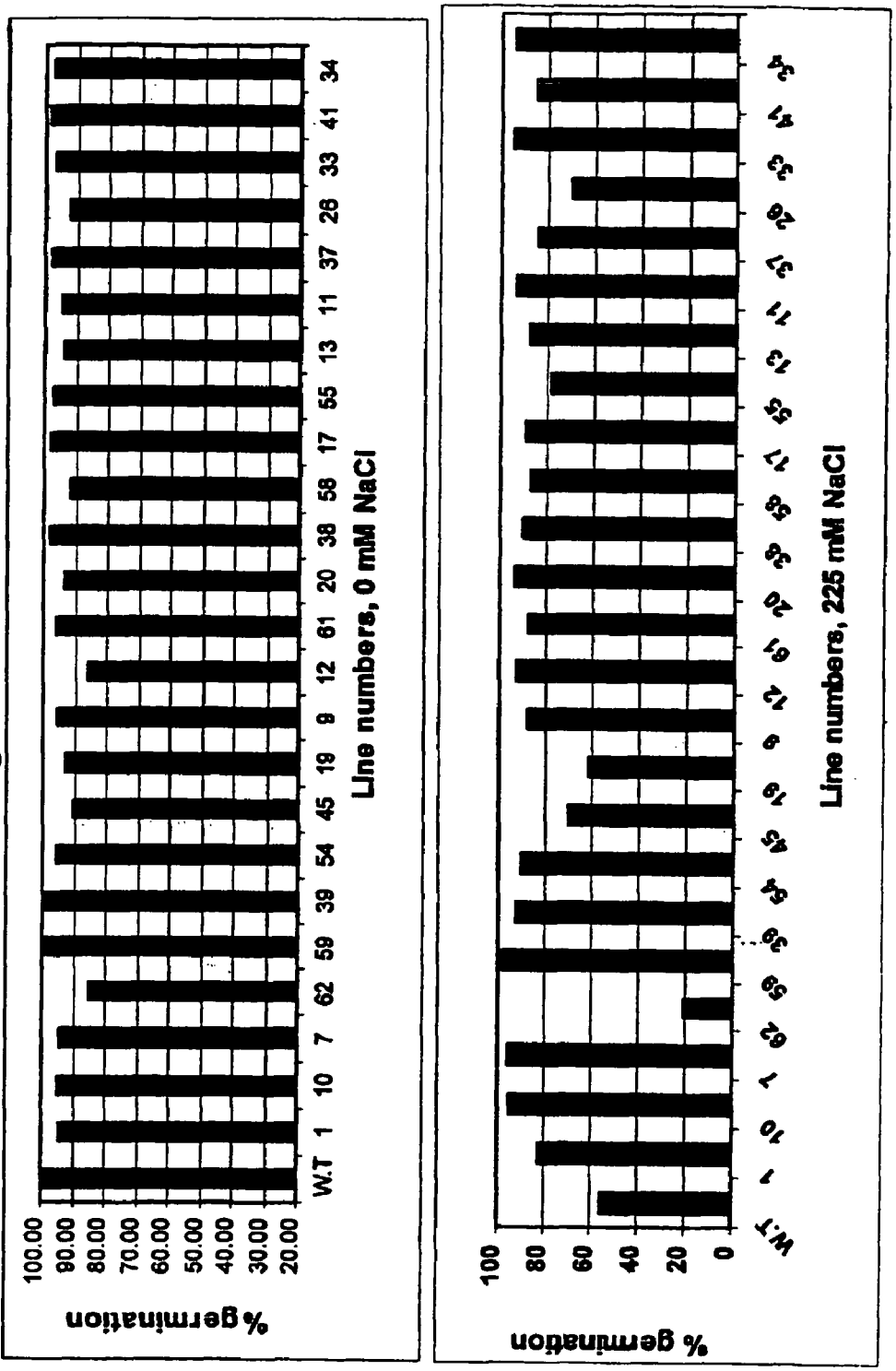
FIG. 6 shows the germination rate of the seeds produced by the selected *A. thaliana* transgenic lines in ½ MS medium with or without 225 mM NaCl.
Figure 7:
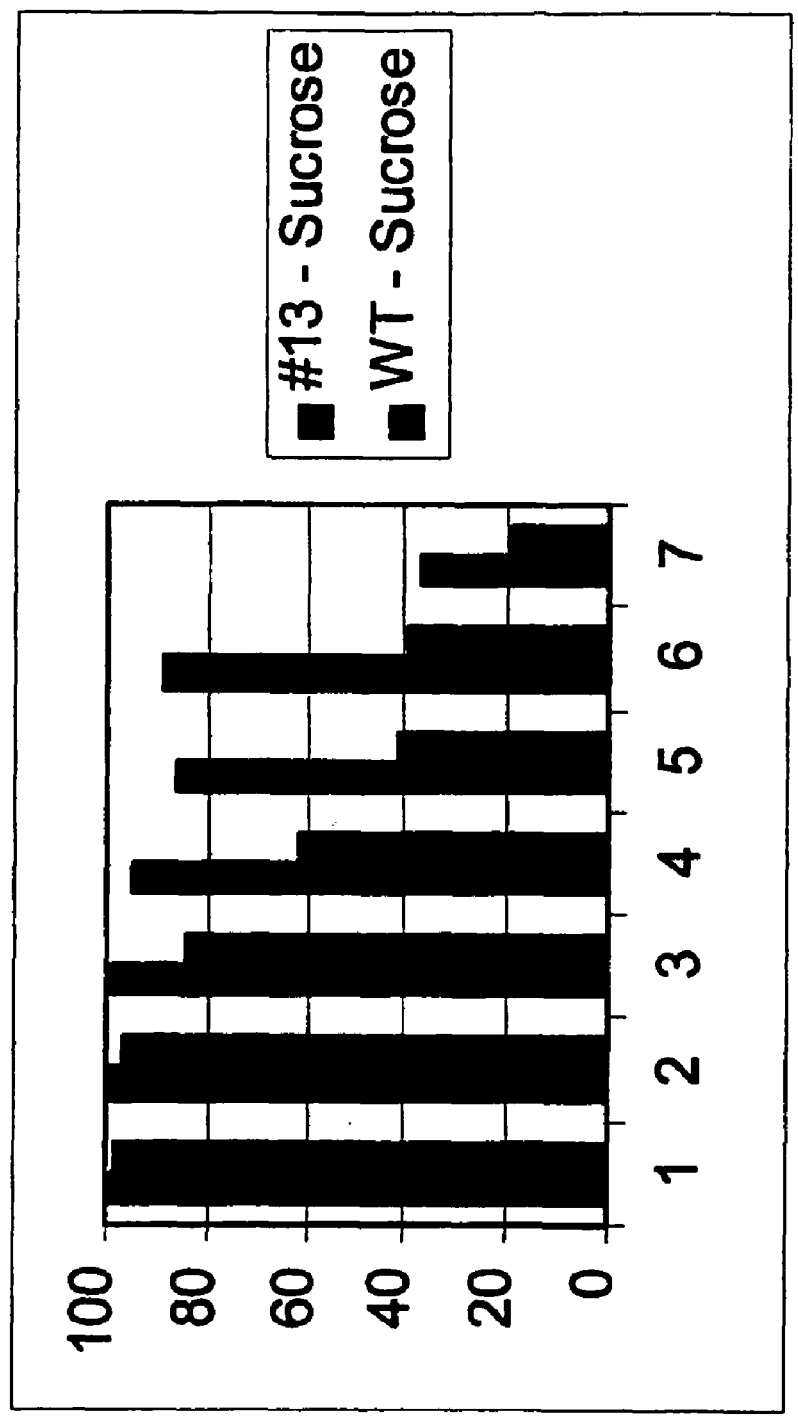
FIG. 7 shows the germination rate of wild type *A. thaliana* and transgenic line #13 seeds in ½ MS media supplemented with various concentrations of NaCl.

The enhanced salinity tolerance could be observed at different developmental stages. Transgenic plant seeds germinated at the same frequency as that of the non-transgenic control plants on ½ MS medium (FIG. 6, upper panel). However, on media with added salt (FIG. 6, lower panel), the wild type germinated at only about 55%, while transgenic lines #54, #58, #7 and #13 germinated at a rate of 90%, 86%, 87% and 95%, respectively. The germination frequencies of line #13 seeds were further evaluated with various NaCl concentrations. As shown in FIG. 7, in all concentrations of NaCl examined, line #13 seeds consistently showed higher germination rates than that of the wild type plant seeds. The most dramatic effect was observed with 250 mM NaCl, in which less than 40% of wild type seeds germinated, while 80% of the line #13 seeds germinated. In neither cases could auxotrophic growth be established from the germinated seeds.

Figure 8:
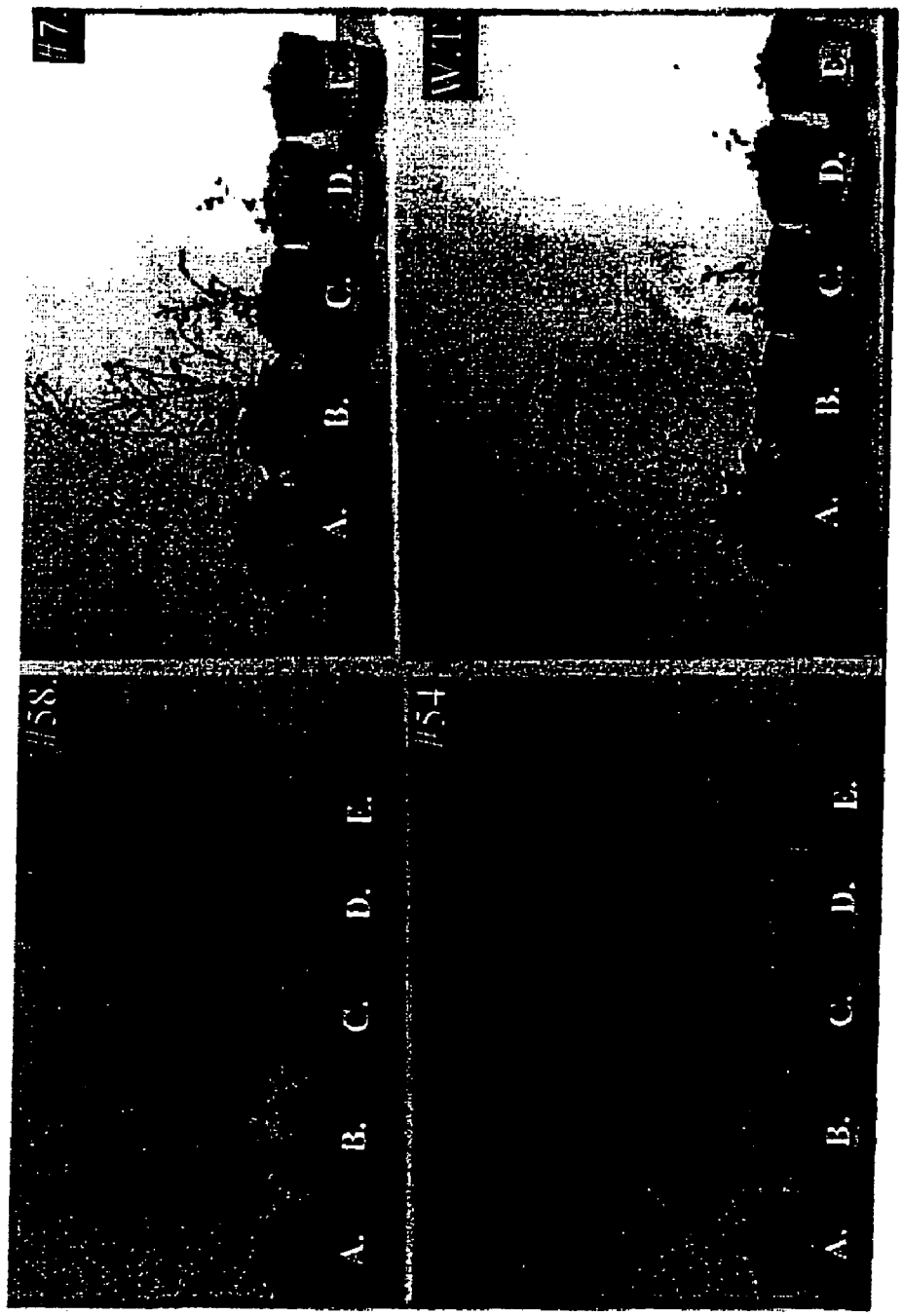
FIG. 8 shows the performance of the soil-grown transgenic plants under various degree of salinity stress as detailed in Experimental Details.

Wild type *A. thaliana* could germinate reasonably well (80%) on medium containing 175 mM NaCl. However, seedling growth and development were severely retarded. In contrast, the growth rate of the transgenic plants was substantially higher. After 6 weeks, wild type plants developed chlorosis on leaf tissues and eventually died, while under the same conditions the transgenic plants still maintained relatively healthy green leaves. Plants growing in soil were also investigated with respect to salinity tolerance. The inventors followed the treatment protocol reported by Apse et al.,[29] designed to mimic field stress conditions. As shown in FIG. 8, the transgenic plants displayed advanced growth and developmental profiles in comparison to those of wild type plants. Most of the wild type plants repeatedly treated with 50 mM NaCl appeared severely stressed with darkened leaf color. The same treatment did not seem to affect the growth and reproduction of the transgenic lines. Wild type plants ceased to grow and eventually died when solutions containing salt at 100 mM were applied, while the majority of the transgenic plants developed to maturity and produced seeds. When a watering regime was carried out to a salt concentration of 150 mM NaCl, the transgenic plants showed apparent stressed phenotype, but were still able to produce seeds, albeit with short siliques and very little seed yield. Plants from line #54 exhibited the most improved salinity among the transgenic lines tested. They produced seeds even when watering reached a salt concentration of 200 mM NaCl.

Example XII gpsA Transgenic *Arabidopsis* had Elevated G3P Content

Figure 9:
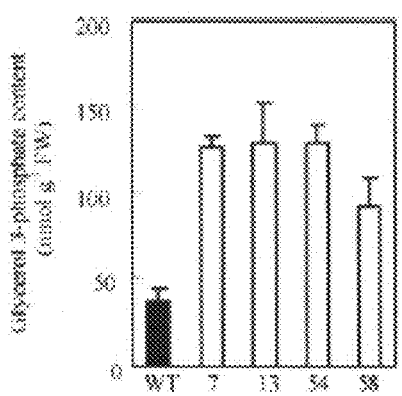
FIG. 9 illustrates the G3P content of gpsA in *Arabidopsis* leaves.

*A. thaliana* L. ecotype Columbia and gpsA transgenic plants were grown in a controlled growth chamber (21° C. day/16° C. night, 55% RH, and 100 umol.m$^{-2}$.s$^{-1}$ PAR) under long-day condition (16 h light/8 h dark photoperiod) for 3 weeks. Rosette leaves were harvested for determining cellular G-3-P content. As show in FIG. 9, the leaf tissues of gpsA plant had a G-3-P content three times that of the wt plants.

Example XIII gpsA Transgenic *Arabidopsis* had a Reduced Phospholipids Molar Ratio in Cellular Membrane Lipid Profile To investigate the impact of an increased G-3-P production on glycerolipid synthesis, major leaf glycerolipid species were separated through 2-D thin-layer chromatography (TLC), and their molar ratio and fatty acid compositions were analyzed in leaf tissues (standard growing condition, see above). The results are summarized in Table 1.

TABLE 1

Fatty acid composition of leaf lipids from wild-type(WT) and gpsA transgenic *Arabidopsis* Values represent the averages of three samples.

| Glycerolipid | Total Polar lipids % | 16:0 | 16:1 | 16:2 | 16:3 | 18:0 | 18:1 | 18:2 | 18:3 | C-16/C-18 |
|---|---|---|---|---|---|---|---|---|---|---|
| MGDG | | | | | | | | | | |
| WT | 35.0 | 1.6 | 1.3 | 2.2 | 29.8 | 0.2 | 1.1 | 3.9 | 59.9 | 0.5 |
| #13 | 39.4 | 2.2 | 1.7 | 2.4 | 37.2 | 0.2 | 1.2 | 3.3 | 51.6 | 0.8 |
| #58 | 41.4 | 2.2 | 1.4 | 2.3 | 39.2 | 0.2 | 1.1 | 2.8 | 50.9 | 0.8 |
| DGDG | | | | | | | | | | |
| WT | 14.0 | 14.6 | | 0.6 | 2.5 | 1.2 | 1.1 | 6.7 | 71.5 | 0.2 |
| #13 | 17.6 | 21.9 | | 0.9 | 4.7 | 1.9 | 1.7 | 6.9 | 61.4 | 0.4 |
| #58 | 17.8 | 19.7 | | 0.8 | 4.8 | 1.8 | 1.3 | 9.7 | 61.6 | 0.3 |

TABLE 1-continued

Fatty acid composition of leaf lipids from wild-type(WT) and gpsA transgenic *Arabidopsis* Values represent the averages of three samples.

| Glycerolipid | Total Polar lipids % | 16:0 | 16:1 | 16:2 | 16:3 | 18:0 | 18:1 | 18:2 | 18:3 | C-16/C-18 |
|---|---|---|---|---|---|---|---|---|---|---|
|  |  |  |  |  | mol % |  |  |  |  |  |
| PG |  |  |  |  |  |  |  |  |  |  |
| WT | 13.4 | 35.1 | 27.1 |  | 1.4 | 5.1 | 9.4 | 21.9 |  | 1.7 |
| #13 | 11.2 | 37.3 | 29.6 |  | 2.9 | 4.2 | 6.1 | 19.9 |  | 2.0 |
| #58 | 10.6 | 41.2 | 26.6 |  | 3.1 | 4.5 | 6.5 | 18.1 |  | 2.1 |
| SL |  |  |  |  |  |  |  |  |  |  |
| WT | 2.9 | 46.9 |  |  | 2.4 | 2.5 | 5.8 | 41.1 |  | 0.9 |
| #13 | 6.9 | 53.3 |  |  | 3.0 | 2.3 | 4.9 | 36.4 |  | 1.1 |
| #58 | 4.0 | 51.0 |  |  | 2.9 | 2.6 | 5.4 | 38.2 |  | 1.0 |
| PC |  |  |  |  |  |  |  |  |  |  |
| WT | 17.5 | 20.1 |  |  | 2.2 | 4.9 | 28.8 | 41.5 |  | 0.3 |
| #13 | 12.5 | 25.9 |  |  | 4.1 | 2.8 | 26.3 | 39.9 |  | 0.4 |
| #58 | 13.0 | 29.4 |  |  | 4.9 | 2.7 | 27.7 | 35.3 |  | 0.4 |
| PE |  |  |  |  |  |  |  |  |  |  |
| WT | 12.3 | 27.3 |  |  | 1.9 | 2.5 | 39.5 | 28.3 |  | 0.4 |
| #13 | 10.5 | 29.2 |  |  | 2.4 | 0.9 | 30.1 | 35.2 |  | 0.4 |
| #58 | 10.1 | 27.1 |  |  | 2.5 | 0.9 | 29.2 | 38.9 |  | 0.4 |
| PI |  |  |  |  |  |  |  |  |  |  |
| WT | 4.2 | 36.8 |  |  | 5.5 | 2.7 | 25.6 | 29.4 |  | 0.6 |
| #13 | 1.9 | 41.3 |  |  | 2.1 |  | 19.9 | 33.5 |  | 0.7 |
| #58 | 3.0 | 43.7 |  |  | 2.8 |  | 18.5 | 35.1 |  | 0.8 |

Sum of 16:1 cis and 16:1 trans fatty acids.

Figure 10:
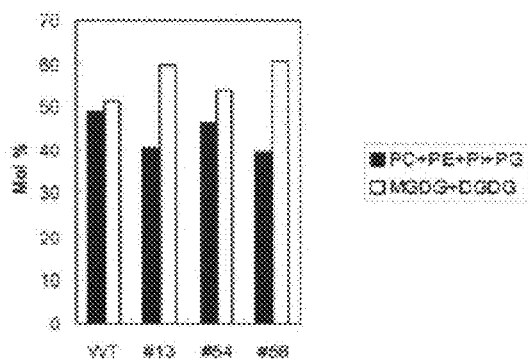
FIG. 10 shows the effect of G3P metabolism on phospholipids content in *Arabidopsis* leaves.

In the gpsA plants, the proportions of non-phospholipid molecules, including monogalactosyldiacylglycerol (MGDG), digalactosyldiacylglycerol (DGDG) and sulfolipid (SL) are substantially increased. The content of phospholipid molecules including phosphatidylcholine (PC), phosphatidylethanolamine (PE), and phosphatidylinostitol (PI) and phosphatidyglycerol (PG) on the other hand, are all reduced. The phospholipid vs. non-phospholipids was decreased (FIG. 10). From the fatty acid composition changes detected in the glycerolipid molecules, it can be inferred that the contribution of the plastidic prokaryotic glycerolipid pathway to total cellular membrane lipid synthesis in the transgenic lines was more than that the wt control.

Example XIV

Figure 11:
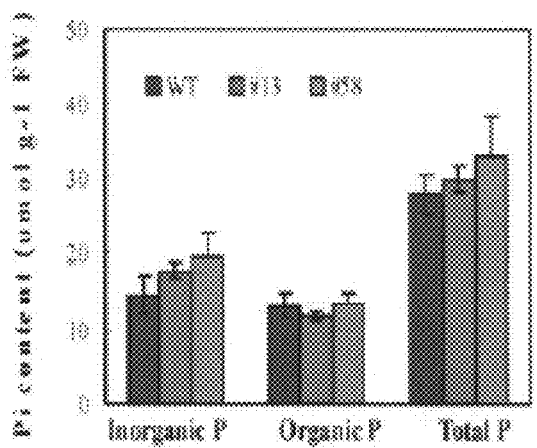
FIG. 11 depicts the phosphorus content in soil growth leaves of gpsA transgenic lines.

Pi Content in gpsA Transgenic *Arabidopsis* Under Standard Growing Conditions Was Not Decreased Since the increased G-3-P would inevitably require more P, it is possible that Pi availability was affected in the transgenic plants. This question was addressed by analyzing P content of the transgenic lines in comparison to that of wild type plants growing in soil under standard conditions. As shown in FIG. 11, the transgenic plants had in fact slightly increased total P content. Importantly, the slight increase in the amount of P in the transgenic plants could be almost entirely accounted for by the increased level of inorganic P. The organic P content remained at a level comparable to that of the wt plants. Thus, the transgenic plants were not under a general inorganic phosphorus (Pi) limitation stress, and that the modified relative contribution of the two glycerolipids pathways was not a result of metabolic response to Pi limitation.

Example XV

G-3-P and Phospholipid Content in Wt Plants Under Pi Limitation Also Show Negative Correlation It was also established that there is an apparent correlation of Pi limitation stress response and cellular G-3-P metabolism in wt plants. G-3-P content of wt plants growing under normal (sufficient P) and Pi-limitation conditions were compared. There was a 5× increase in G-3-P content in the leaf of wt plant under inorganic P limitation (0.1 mM) condition (compared with Pi supply at 1 mM) FIG. 12A.

Figure 12:
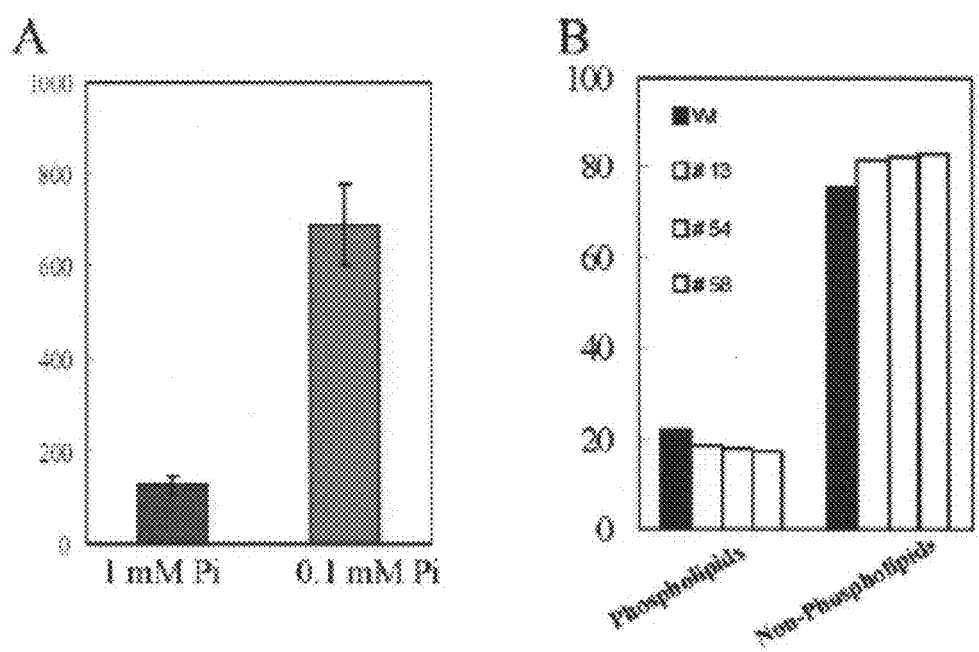
FIG. 12 illustrates G3P and phospholipids content of *Arabidopsis* developed in low and high Pi medium

Under Pi limitation conditions, both the wt and the transgenic lines have reduced phospholipids content. Thus, there is a negative correlation between G-3-P content and the proportion of phospholipids in cellular membrane systems in both wt and the transgenic lines (FIG. 12B).

Example XVI

Enhanced Growth of gpsA Transgenic *Arabidopsis* Under Pi Limitation Condition

Figure 13:
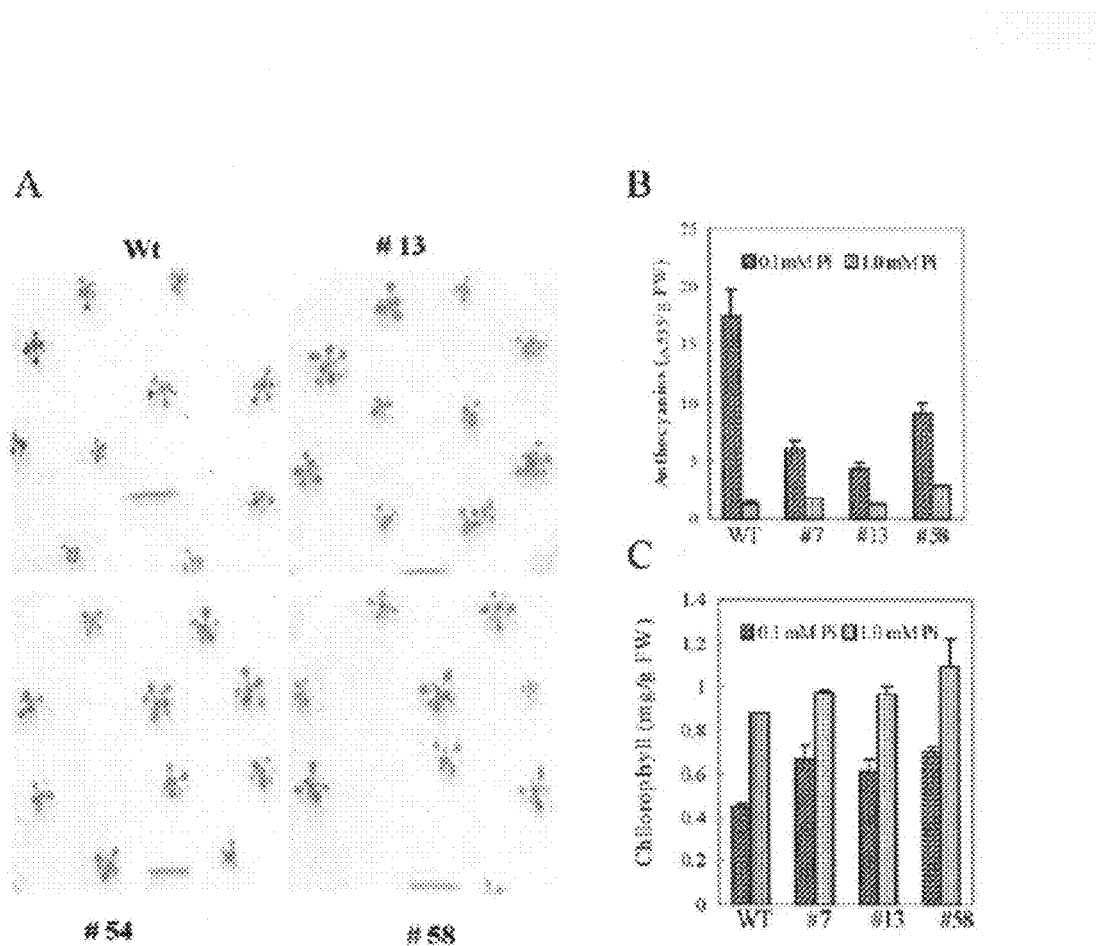
FIG. 13 depicts that a transgenic *Arabidopsis* gpsA line is tolerant to low Pi stress.

When directly germinating seeds on low Pi (0.1 mM) medium, after 3 weeks, the gpsA transgenic *Arabidopsis* grew better than wt plants (FIG. 13A). Furthermore, wt plants displayed purple color, an indication of anthocyanin accumulation which is often observed under low Pi supply. In contrast, the gpsA lines performed much better, displaying green leaves with no visible sign of anthocyanin accumulation. When the anthocyanin content was quantified, the level in wt was found to be 2-3 times high than that in the gpsA lines (FIG. 13B). In contrast, the chlorophyll content in wt was 45% lower than gpsA line (FIG. 13C). These results indicated that the gpsA lines were not suffering from low Pi-availability at the same degree as that of the wt plants.

Figure 14:
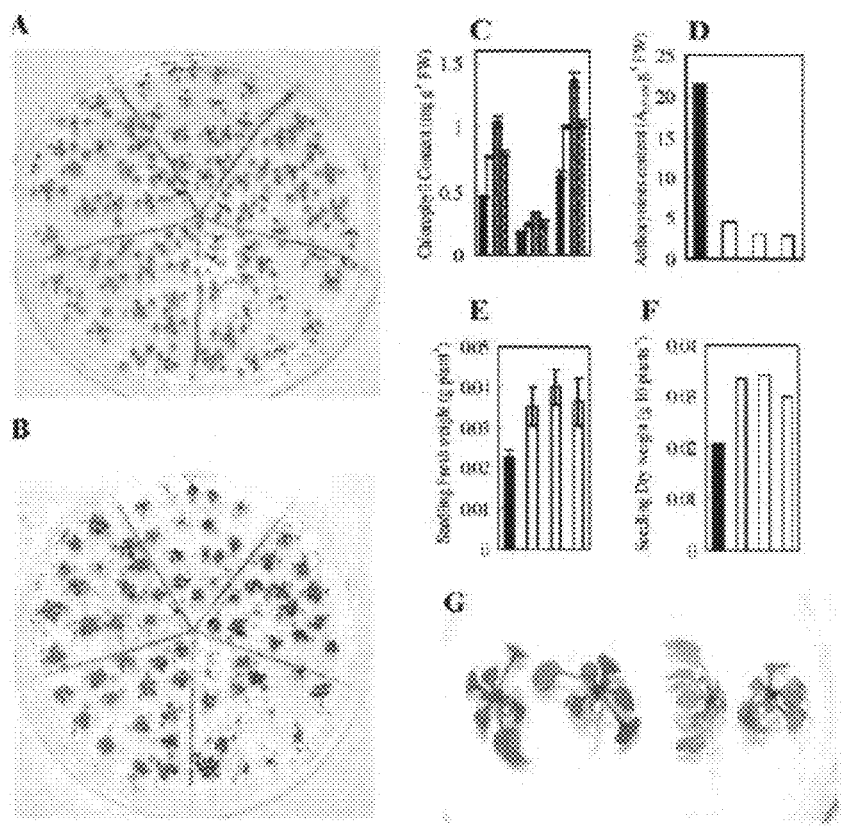
FIG. 14 is another embodiment showing that the *Arabidopsis* gpsA line is tolerant to low Pi stress.

When seedlings were raised in normal Pi condition for 10 days and transplanted to low Pi medium for another 10 days, similar results were obtained. As show in FIG. 14A, gpsA line demonstrated better growth rate. The chlorophyll content of the gpsA lines was 50% higher than that of the wt plants (FIG. 14C), and the anthocyanins content of gpsA line was 4 times lower than that of the wt plants (FIG. 14D). After 25 days on low Pi, the trend of better performance by the gpsA line continued (FIG. 14B). When the fresh weight and dry weight of gpsA lines were assessed, there was a consistently a 40% to 45% increased as compared with wt plants (FIGS. 14E and 14F). It has been known that plant accumulate starch under Pi limitation condition. Accordingly, higher level of starch accumulation was observed in wt plants under low Pi condition when compared to gpsA plants (FIG. 14G).

Figure 15:
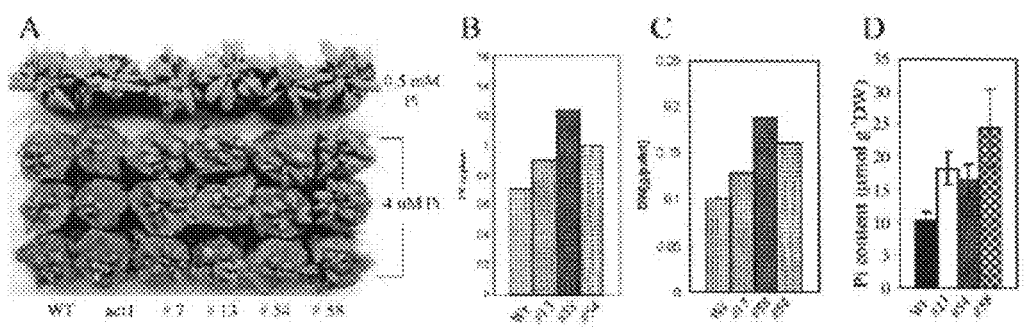
FIG. 15 in an additional embodiment showing that the *Arabidopsis* gpsA line is tolerant to low Pi stress. Seeds were grown in rock wool for 2 weeks under high Pi condition (0.5 mM), and seedlings were transplanted to a reduced Pi content condition (4 μm) for 10 days.

When plants were hydroponically grown in rock wool under low Pi (4 µM) (0.124 ppm) condition for 3 weeks, the fresh weight and dry weight of gpsA plants were also 30%-70% higher than that of the wt plants (FIGS. 15B and 15C). Furthermore, higher levels of inorganic Pi content were detected in gpsA leaves compared to wt plants (FIG. 15D).

Example XVII

Deficiency in the Endogenous G-3-P Dehydrogenase in *Arabidopsis* Leads to a Compromised Growth Under Pi-limitation When Compared to Wt Plants

Figure 16:
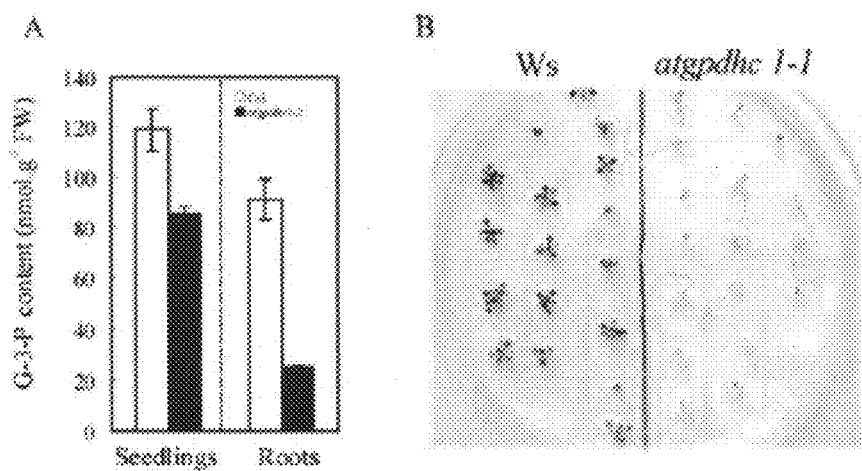
FIG. 16 depicts the *Arabidopsis* mutant atgpdhcl-1 deficiency in glycerol-3-phosphate dehydrogenase gene (AtGPDHc) has low G3P content and is sensitive to low Pi stress.

*Arabidopsis* mutant atgpdhcl-1 (ecotype Wassilewskija) with T-DNA insertions interrupting the *Arabidopsis* endogenous G-3-P dehydrogenase gene, AtGPDHcl, was identified through screening the T-DNA tagged population available at the University of Wisconsin. This mutant has the G-3-P dehydrogenase activity, and hence the amount of cellular G-3-P, at a level even lower than that of the wt plants. It was though that this mutant should be hyper-sensitive to Pi-starvation, and perform worse than wt plants when Pi is limiting. It was determined that growth of atgpdhcl-1 mutant line under low Pi condition, as shown in FIG. 16A, had a significant reduction in total G-3-P content which was detected in seedling and root of atgpdhcl mutants. The reduction was also associated with a decreased growth rate compared to control plant Ws. After 60 days, atgpdhcl mutants were all died, but their control plant Ws was still viable, albeit severely stressed.

Example XVIII

Enhanced Growth of gpsA Transgenic Canola Under Pi-limitation Conditions

Figure 17:
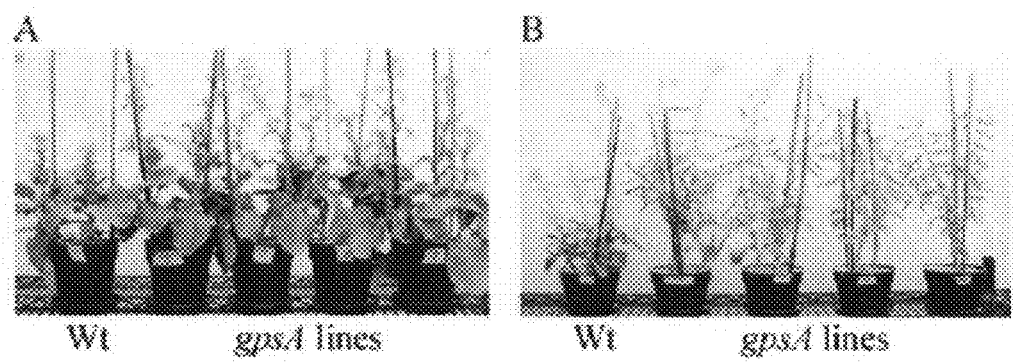
FIG. 17 illustrates that gpsA transgenic canola is tolerant to low Pi stress. Seedlings are grown in sand and watered with a +Pi solution (100 ml/pot) every 2 days for 3 weeks (FIG. 17A).

*B. napus* is an important oil crop in the world and phosphorus requirements for good yield of canola are greater than those for wheat or barley. Therefore, transgenic canola with the gpsA gene construct was generated, and its performance was assessed with regard to low Pi tolerance. As shown in FIGS. 17A and 17B, when plants were subjected to low Pi condition in sand culture, the gpsA canola plants exhibited a clear advantage in growth than the wt control, and also reached flowering stage earlier. Significantly, the seed yields in gpsA canola plants were substantially higher than wt plants (FIG. 17B).

Figure 18:
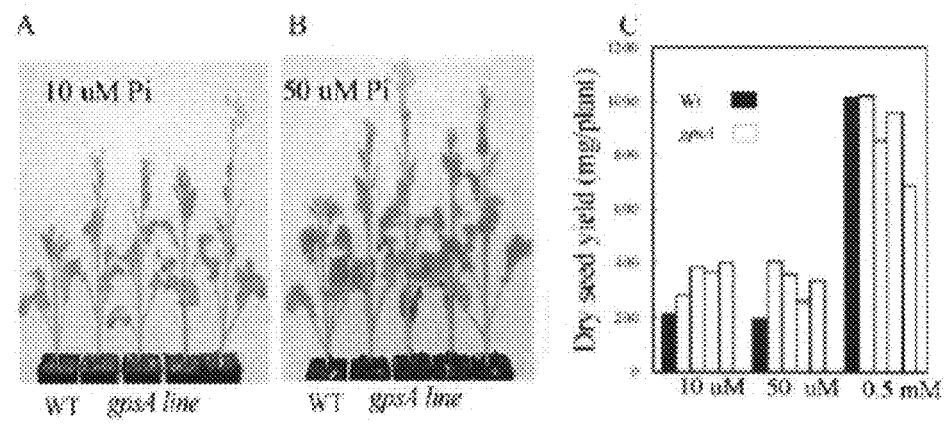
FIG. 18 illustrates another embodiment showing that gpsA transgenic canola are tolerant to low Pi stress. Seedlings grown for 4 days in sand are transplanted to medium containing 0.5 mM Pi for 7 days, then the medium is changed to 10 μm and 50 μm every week for 2 weeks. After 2 weeks, the medium is changed to a non-Pi medium every week until the plants mature.

The benefit of introducing the gpsA gene to canola for low Pi growth was further verified through hydroponics culture. Similar to sand culture, the gpsA canola plants developed much better stems and leaves; flowered early (FIGS. 18A and 18B); and the seeds yield of gpsA plants were 50-100% higher in both 10 µM (0.31 ppm) and 50 µM (1.55 ppm) (low) Pi condition (FIG. 18C).

Figure 19:
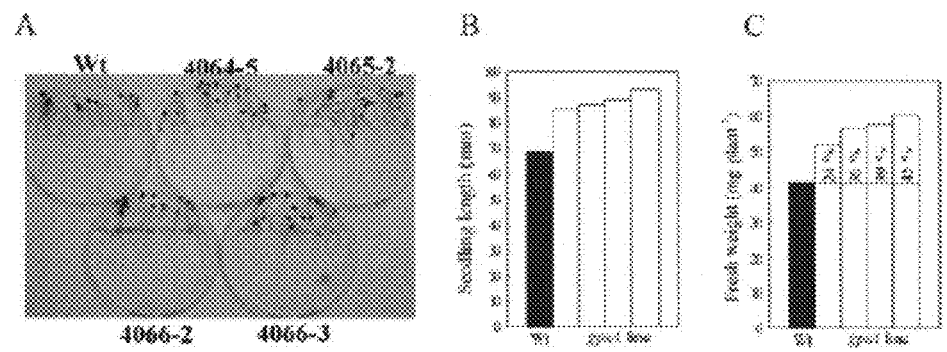
FIG. 19 shows that gpsA transgenic canola developed a large plant structure from an early growth stage under low Pi and low temperature conditions. The seeds were planted in filter paper and water with a –Pi nutrients solution under 8° C. for 16 days.

An adequate supply of soil phosphorus under cold climate has been recognized as a major limiting factor for plant to establish a strong, healthy rooting system in early growth stages, which will bear consequence to overall use of moisture and nutrients. Promoting early vegetative growth and the development of larger seedling is hence an important agronomic trait. In addition, early growth results in earlier and more uniform flowering, thus enhancing pod and seed development with higher yields, and also better able to withstand stresses from biotic and abiotic stresses. Soil temperature is a key factor for early seedling growth, generally, temperature below 10° C. results in progressively poorer germination and emergence. It was determined that the gpsA canola seedling response to combined low Pi and low temperature conditions. As show in FIG. 19A, gpsA canola developed larger seedling in a manner that is consistent with an improved capacity to establish early growth. There was a 25-45% increase in seedling length and fresh weight (FIGS. 19B and 19C) in the gpsA seedlings than wt plant under low Pi and low temperature condition.

Example XIX

Identification of gpsA Genes in Bacteria

The sequences of gpsA genes that are homologous to the *E. coli* gpsA gene are identified by sequence alignment using the computer program DNAstar™ or the blast program that is known and readily commercially available from the National Center for Biotechnology Information (NCBI) available on the Internet.

Example XX

Construction of Plant Transformation Vectors for gpsA Genes of the Other Bacteria Primers TTAGTGGCTGCTGCGCTC (GPSA3, SEQ ID NO: 3) and AACAATGAACCAACGTAA (GPSA5, SEQ ID NO: 4), complementary to the sequences corresponding to the 3' and 5' end of the gpsA gene, respectively, in *E. coli* are used for PCR amplifications with template DNA isolated from strains of *Shigella flexneri, Salmonella typhimurium, Salmonella enterica, Yersinia pestis, Yersinia pseudotuberculosis, Serratia marcescens, Photorhabdus luminescens* and *Erwinia carotovora* including wt gpsA genes. The PCR products are purified with QIAquick™ PCR purification Kit (Qiagen™) and fully sequenced.

Example XXI

Construction of Plant Transformation Vectors

Primers GAGAGCTCTTAGTGGCTGCTGCGCTC (GPSA31, SEQ ID NO: 5) and GAAGAAGGATCCAA-CAATGAACCAACGTAA (GPSA51, SEQ ID NO: 6) complementary to the 3' and 5' end of the gpsA gene, respectively, in *E. coli* and including, at the 5' end of GPSA31, a SacI restriction site and a BamHI restriction site at the 5' end of GPSA5 are used to PCR amplify the gpsA sequences of *S.* flexneri (SEQ ID NO: 7), *S. typhimurium* (SEQ ID NO: 9), *S. enterica* (SEQ ID NO: 11), *Y. pestis* (SEQ ID NO: 13), *Y. pseudotuberculosis* (SEQ ID NO: 15), *S. marcescens* (SEQ ID NO: 17), *P. luminescens* (SEQ ID NO: 19) and *E. carotovora* (SEQ ID NO: 21). The PCR products are purified with QIAquick™ PCR purification Kit (Qiagen) and are digested with SacI/BamHI. The SacI/BamHI digested gpsA2$^{FR}$ DNA fragments are inserted into the *Agrobacterium* binary vector-pBI121 (Clontech), thus, replacing the SacI/BamHI region of the GUS gene. The resultant plant transformation vector includes an expression cassette containing the gpsA encoding region of *S. flexneri, S. typhimurium, S. enterica, Y. pestis, Y. pseudotuberculosis, S. marcescens, P. luminescens* and *E. carotovora* driven by the constitutive 35S promoter. Its 3' end is flanked by the NOS terminator. The junction region between the 35S promoter and the gpsA encoding sequence for each vector including the gpsA encoding region of *S. flexneri, S. typhimurium, S. enterica, Y. pestis, Y. pseudotuberculosis, S. marcescens, P. luminescens* and *E. carotovora* is confirmed through sequencing. The gpsA protein of *S. flexneri* (SEQ ID NO: 8), *S. typhimurium* (SEQ ID NO: 10), *S. enterica* (SEQ ID NO: 12), *Y. pestis* (SEQ ID NO: 14), *Y. pseudotuberculosis* (SEQ ID NO: 16), *S. marcescens* (SEQ ID NO: 18), *P. luminescens* (SEQ ID NO: 20) and *E. carotovora* (SEQ ID NO: 22) are, thus, expressed in plant tissues including vegetative and reproductive (seed) tissues once the gene expression cassette is incorporated into the plant genome.

Example XXII

Plant Growth Conditions

*A. thaliana* and canola are chosen as plant hosts to test the effect of the gpsA genes for *S. flexneri, S. typhimurium, S. enterica, Y. pestis, Y. pseudotuberculosis, S. marcescens, P. luminescens* and *E. carotovora*, as well as gpsA genes having conservative mutations. All *A. thaliana* and canola control and transgenic plants are grown at the same time, in controlled growth chambers, under 16 hr fluorescent illumination (150-200 μE/m/sec), 8 hr dark at 22° C., as described previously.[19]

Example XXIII

Plant Transformation

Plasmids including the gpsA gene of each of *S. flexneri* (SEQ ID NO: 7), *S. typhimurium* (SEQ ID NO: 9), *S. enterica* (SEQ ID NO: 11), *Y. pestis* (SEQ ID NO: 13), *Y. pseudotuberculosis* (SEQ ID NO: 15), *S. marcescens* (SEQ ID NO: 17), *P. luminescens* (SEQ ID NO: 19) and *E. carotovora* (SEQ ID NO: 21) as well as conservative mutations thereof are introduced into *A. tumefaciens* strain GV3101 bearing helper nopaline plasmid pMP90, via electroporation. Wild type *A. thaliana* plants of ecotype Columbia and canola are grown. One week after bolting, plants are vacuum-infiltrated overnight with a suspension of *A. tumefaciens* strain GV3101 harboring the plasmids including the gpsA gene of each of *S. flexneri* (SEQ ID NO: 7), *S. typhimurium* (SEQ ID NO: 9), *S. enterica* (SEQ ID NO: 11), *Y. pestis* (SEQ ID NO: 13), *Y. pseudotuberculosis* (SEQ ID NO: 15), *S. marcescens* (SEQ ID NO: 17), *P. luminescens* (SEQ ID NO: 19), *E. carotovora* (SEQ ID NO: 21) and conservative mutations thereof.

After infiltration, plants are grown to set seeds (T1). Dry seeds (T1) are harvested in bulk and screened on selective medium with 50 mg/L kanamycin. After two to three weeks on selective medium, kanamycin resistant seedlings (T1) which appear as green are transformed to soil to allow growth to maturity. Seeds (T2) from the T1 plants are harvested and germinated on kanamycin plates to test segregation ratios. A typical single gene insertion event gives rise to a kanamycin resistant/sensitive ratio of 3:1. To confirm the integration of the gpsA gene, DNA is isolated from selected transgenic lines and Southern blot analysis is performed with probes prepared with gpsA DNA. Total RNA is also isolated for Northern analysis to confirm the expression of the gpsA gene of each of *S. flexneri* (SEQ ID NO: 7), *S. typhimurium* (SEQ ID NO: 9), *S. enterica* (SEQ ID NO: 11), *Y. pestis* (SEQ ID NO: 13), *Y. pseudotuberculosis* (SEQ ID NO: 15), *S. marcescens* (SEQ ID NO: 17), *P. luminescens* (SEQ ID NO: 19), *E. carotovora* (SEQ ID NO: 21) and conservative mutations thereof.

Example XXIV

Growth of gpsA Transgenic *A. thaliana* and Canola Under Inorganic P Limitation Condition The transgenic wild type *A. thaliana* plants of ecotype Columbia and canola including the gpsA genes of *S. flexneri* (SEQ ID NO: 7), *S. typhimurium* (SEQ ID NO: 9), *S. enterica* (SEQ ID NO: 11), *Y. pestis* (SEQ ID NO: 13), *Y. pseudotuberculosis* (SEQ ID NO: 15), *S. marcescens* (SEQ ID NO: 17), *P. luminescens* (SEQ ID NO: 19), *E. carotovora* (SEQ ID NO: 21) and conservative mutations thereof are grown in soil having a reduced P content (less than 20 ppm) or on low Pi medium (0.1 mM) (about 3.1 ppm) medium. After 3 weeks, the growth of the wt plants are compared to the transgenic plants, and anthocyanin content and chlorophyll content are quantified.

The plants are also hydroponically grown in rock wool under low Pi (4 μM) (about 0.124 ppm) condition for 3 weeks. The fresh weight, dry weight and inorganic content of Pi of wt and transgenic gpsA plants are also determined.

Although the present invention has been shown and described with respect to various exemplary embodiments, various additions, deletions, and modifications that are obvious to a person of ordinary skill in the art to which the invention pertains, even if not shown or specifically described herein, are deemed to lie within the scope of the invention as encompassed by the following claims. Further, features or elements of different embodiments may be employed in combination.

REFERENCES (INCORPORATED HEREIN BY REFERENCE)

[1] Gee et al., (1988) *Plant Physiol.* 86, 98-103; Gee et al., (1988) *Plant Physiol.* 87, 379-383.

[2] Kirsh et al., (1992) *Plant Physiol.* 100, 352-359.

[3] Hsu and Fox (1970) *J. Bacterial.* 103, 410-416; Bell (1974) *J. Bacterial.* 117, 1065-1076.

[4] Ansell et al., (1997), *EMBO J.* 16, 2179-2187.

[5] Brown (1990), in *Micorbial Water Stress Physiology, Principles and Perspectives*. John Wiley & Sons, New York.

[6] Larsson et al., (1993), *Mol. Microbiol.* 10, 1101-1111.

[7] Ansell et al., (1997), *EMBO J.* 16, 2179-2187.

[8] Husic and Tolbert, (1986), *Plant Physiol.* 82, 594-596; Ben-Amotz and Avron, (1983), *Annu Rev Microbiol.* 37,95-119.

[9] Hausmann et al., (1995). *In Plant Lipid Metabolism*, (Kader, J. C., and Mazliak, P., eds), pp53-536, Kluwer Academic Publishers.

[10] Bell and Cronan (1975), *J. Biol. Chem.* 250, 7147-7152.
[11] Datla R S, Hammerlindi J K, Panchuk B, Pelcher L E, Keller W. (1992). *Modified binary plant transformation vectors with the wild-type gene encoding NPTII.; Gene* 122:383-384.
[12] Frisch D A, Harris-Hailer L W, Yokubaitis N T, Thomas T L, Hardin S H, Hall T C. (1995). Complete sequence of the binary vector Bin19; *Plant Mol Biol* 27:405-409.
[13] Roesler K, Shintani D, Savage L, Boddupalli S, Ohlrogge J B (1997) *Targeting of the Arabidopsis homomeric acetyl-coenzyme A carboxylase to plastids of rapeseeds; Plant Physiol* 113: 75-81.
[14] Meyerowitz, E. M. and Chang, C. (1985) *Molecular biology of plant growth and development: Arabidopsis thaliana as an experimental system. In: Developmental Biology*, Vol. 5, Plenum Press, NY., pp. 353-366.
[15] Meyerowitz, E. M. (1987) *Arabidopsis thaliana. Ann. Rev. Genet.* 21: 93-111.
[16] Goodman, H. M., Ecker, J. R. and Dean, C. (1995) *The genome of Arabidopsis thaliana. Proc. Nat'l. Acad. Sci. USA* 92: 10831-10835.
[17] Lagercrantz, U., Putterill, J., Coupland, G. and Lydiate, D. (1996) *Comparative mapping in Arabidopsis and Brassica, fine scale genome collinearity and congruence of genes controlling flowering. Plant J.* 9: 13-20.
[18] see for example: Zou et al., U.S. Pat. No. 6,051,755, Apr. 18, 2000.
[19] Katavic et al., (1995), *Plant Physiol.* 108, 399-409.
[20] Bechtolds et al., (*C.R. Acad. Sci. Paris, Sciences de Ia vie/Life sciences* 316, 1194-1199.
[21] Katavic et al., (1995) *Plant Physiol.* 108:399-409.
[22] Apse et al., (1999) *Science* 285, 1256-1258.
[23] Murashige and Skoog (1962), *Physiol Plant* 15: 473-497.
[24] *J Biol. Chem.* (1969), 244, 3316-3333.
[25] Cronan and Bell; (1974), 1. *Bacteriol.* 118, 598-605.
[26] Ye and Larson (1988), *J. Bacteriol.,* 170, 4209-4215.
[27] Bell and Cronan (1975), *J. Biol. Chem.* 250, 7147-7152.
[28] Gardiner et al., (1982), *Plant Physiol.* 70, 1316-1320.
[29] Apse et al., (1999) *Science* 285, 1256-1258.

What is claimed is:

1. A process for harvesting a transgenic seed, the process comprising:
   planting a transgenic plant, plant seed or progeny thereof in a soil having a phosphorus content of less than about 20 ppm of phosphorus; wherein the transgenic plant, plant seed or progeny thereof has been transformed with a heterologous polynucleotide sequence encoding a bacterial NAD+ dependent glycerol-3-phosphate dehydrogenase polypeptide selected from the group consisting of SEQ ID NO:2, SEQ ID NO:8, SEQ ID NO:10, SEQ ID NO:12, SEQ ID NO:14, SEQ ID NO:16, and SEQ ID NO:22;
   expressing said polypeptide in the transgenic plant, plant seed or progeny thereof;
   growing the transgenic plant, plant seed or progeny thereof to maturity in the soil; and
   harvesting seed from the mature transgenic plant, plant seed or progeny thereof.

2. The process according to claim 1, wherein the transgenic plant, plant seed or progeny thereof has been transformed with the heterologous polynucleotide sequence of SEQ ID NO:1.

3. The process according to claim 2, further comprising steps of selecting a plant cell transformed with the heterologous polynucleotide sequence, and regenerating the plant cell into the transgenic plant.

4. The process according to claim 1, wherein growing the transgenic plant, plant seed or progeny thereof to maturity in the soil occurs for at least 60 days.

5. The process according to claim 1, further comprising extracting oil from the harvested seed.

6. A transgenic canola plant, seed or progeny thereof, comprising: a genome; said genome transformed with a heterologous polynucleotide sequence encoding a bacterial NAD+ dependent glycerol-3-phosphate dehydrogenase polypeptide selected from the group consisting of SEQ ID NO:2, SEQ ID NO:8, SEQ ID NO:10, SEQ ID NO:12, SEQ ID NO:14, SEQ ID NO:16, and SEQ ID NO:22; and a promoter operatively linked to the heterologous polynucleotide sequence; and wherein the transgenic canola plant, seed or progeny thereof expresses said polypeptide so that the transgenic canola plant, seed or progeny thereof is capable of growing in a soil having a phosphorus content of less than 20 ppm of phosphorus in comparison to a wild type canola plant, seed or progeny thereof grown under identical conditions.

7. The transgenic canola plant, seed or progeny thereof of claim 6, wherein the heterologous polynucleotide sequence is SEQ ID NO:1.

8. A method for producing a plant, plant seed or progeny thereof, comprising:
   obtaining a soil having a phosphorus content of less than about 20 ppm of phosphorus; and a transgenic plant, plant seed or progeny thereof transformed with a heterologous gene encoding a bacterial NAD+ dependent glycerol-3-phosphate dehydrogenase polypeptide selected from the group consisting of SEQ ID NO:2, SEQ ID NO:8, SEQ ID NO:10, SEQ ID NO:12, SEQ ID NO:14, SEQ ID NO:16, and SEQ ID NO:22;
   expressing said polypeptide in the transgenic plant, plant seed or progeny thereof; and
   wherein the transgenic plant, plant seed or progeny thereof is capable of growing for about 60 days in the soil having the phosphorus content of less than about 20 ppm of phosphorus in comparison to a wild type plant, plant seed or progeny thereof of the same species grown under identical conditions.

9. A method for reducing an amount of phosphorus required to grow a crop plant, the method comprising:
   obtaining a transgenic crop plant, plant seed or progeny thereof transformed with a heterologous gene encoding a bacterial NAD+ dependent glycerol-3-phosphate dehydrogenase polypeptide selected from the group consisting of SEQ ID NO:2, SEQ ID NO:8, SEQ ID NO:10, SEQ ID NO:12, SEQ ID NO:14, SEQ ID NO:16, and SEQ ID NO:22;
   expressing said polypeptide in the transgenic crop plant, plant seed or progeny thereof; and
   wherein the transgenic crop plant, plant seed or progeny thereof is capable of growing for at least 60 days in a soil having phosphorus content of less than 20 ppm of phosphorus in comparison to a wild type crop plant, plant seed or progeny thereof of the same species grown under identical conditions; and planting the transgenic crop plant, plant seed or progeny thereof in the soil.

10. A crop growing in a field, the crop comprising at least one transgenic plant transformed with a heterologous polynucleotide sequence encoding a bacterial NAD+ dependent glycerol-3-phosphate dehydrogenase polypeptide selected from the group consisting of SEQ ID NO:2, SEQ ID NO:8, SEQ ID NO:10, SEQ ID NO:12, SEQ ID NO:14, SEQ ID NO:16, and SEQ ID NO:22; and wherein the transgenic plant expresses said polypeptide so that the transgenic plant is capable of growing for at least 60 days in a soil having a phosphorus content of less than 20 ppm of phosphorus in comparison to a wild type plant, seed or progeny thereof of the same species grown under identical conditions.

11. A method of growing a plant in a soil having a phosphorus content of less than about 20 ppm of phosphorus, wherein the plant has been genetically modified, in comparison to a wild type plant of the same species, to comprise a heterologous gene encoding a bacterial NAD+ dependent glycerol-3-phosphate dehydrogenase polypeptide selected from the group consisting of SEQ ID NO:2, SEQ ID NO:8, SEQ ID NO:10, SEQ ID NO:12, SEQ ID NO:14, SEQ ID NO:16, and expressing said polypeptide in the genetically modified plant so that the genetically modified plant grows beyond sixty days in said soil in comparison to a wild type plant of the same species grown under identical conditions.

12. A transgenic crop plant, plant seed or progeny thereof comprising: a heterologous polynucleotide sequence transformed into the genome of the transgenic crop plant, plant seed or progeny thereof, wherein the heterologous polynucleotide sequence encodes a bacterial NAD+ dependent glycerol-3-phosphate dehydrogenase polypeptide selected from the group consisting of SEQ ID NO:2, SEQ ID NO:8, SEQ ID NO:10, SEQ ID NO:12, SEQ ID NO:14, SEQ ID NO:16, and wherein the transgenic crop plant, plant seed or progeny thereof expresses said polypeptide so that the transgenic crop plant, plant seed or progeny thereof is capable of growing in a soil having a phosphorus content of less than about 20 ppm of phosphorus in comparison to a wild type crop plant, plant seed or progeny thereof of the same species grown under identical conditions.

13. The transgenic crop plant, plant seed or progeny thereof according to claim 12, wherein the transgenic crop plant, plant seed or progeny thereof is selected from the group consisting of *Borago officinalis*, *Brassica* species, *Cannabis sativa*, *Carthamus tinctorius*, *Cocos nucifera*, *Crambe abyssinica*, *Cuphea* species, *Elaeis guinensis*, *Elaeis oleifera*, *Glycine max*, *Soja max*, *Gossypium hirsutum*, *Gossypium barbadense*, *Gossypium herbaceum*, *Helianthus annuus*, *Linum usitatissimum*, *Oenothera biennis*, *Olea europaea*, *Oryza sativa*, *Ricinus communis*, *Sesamum indicum*, *Triticum* species, and *Zea maize*.

14. The transgenic crop plant, plant seed or progeny thereof according to claim 12, wherein the heterologous polynucleotide sequence is SEQ ID NO:1.

* * * * *

SEQUENCE LISTING

<160> NUMBER OF SEQ ID NOS: 22

<210> SEQ ID NO 1
<211> LENGTH: 1020
<212> TYPE: DNA
<213> ORGANISM: Escherichia coli

<400> SEQUENCE: 1

```
atgaaccaac gtaatgcttc aatgactgtg atcggtgccg gctcgtacgg caccgctctt      60
gccatcaccc tggcaagaaa tggccacgag gttgtcctct ggggccatga ccctgaacat     120
atcgcaacgc ttgaacgcga ccgctgtaac gccgcgtttc tccccgatgt gccttttccc     180
gatacgctcc atcttgaaag cgatctcgcc actgcgctgg cagccagccg taatattctc     240
gtcgtcgtac ccagccatgt ctttggtgaa gtgctgcgcc agattaaacc actgatgcgt     300
cctgatgcgc gtctggtgtg ggcgaccaaa gggctggaag cggaaaccgg acgtctgtta     360
caggacgtgg cgcgtgaggc cttaggcgat caaattccgc tggcggttat ctctggccca     420
acgtttgcga aagaactggc ggcaggttta ccgacagcta tttcgctggc ctcgaccgat     480
cagacctttg ccgatgatct ccagcagctg ctgcactgcg gcaaaagttt ccgcgtttac     540
agcaatccgg atttcattgg cgtgcagctt ggcggcgcgg tgaaaaacgt tattgccatt     600
ggtgcgggga tgtccgacgg tatcggttt ggtgcgaatg cgcgtacggc gctgatcacc     660
cgtgggctgg ctgaaatgtc gcgtcttggt gcggcgctgg gtgccgaccc tgccacctt     720 atgggcatgg cggggcttgg cgatctggtg cttacctgta ccgaaaacca gtcgcgtaac     780
cgccgttttg gcatgatgct cggtcagggc atggatgtac aaagcgcgca ggagaagatt     840
ggtcaggtgg tggaaggcta ccgcaatacg aaagaagtcc gcgaactggc gcatcgcttc     900
ggcgttgaaa tgccaataac cgaggaaatt tatcaagtat tatattgcgg aaaaaacgcg     960
cgcgaggcag cattgacttt actaggtcgt gcacgcaagg acgagcgcag cagccactaa    1020
```

<210> SEQ ID NO 2
<211> LENGTH: 339
<212> TYPE: PRT
<213> ORGANISM: Escherichia coli -continued

```
<400> SEQUENCE: 2

Met Asn Gln Arg Asn Ala Ser Met Thr Val Ile Gly Ala Gly Ser Tyr
1               5                   10                  15

Gly Thr Ala Leu Ala Ile Thr Leu Ala Arg Asn Gly His Glu Val Val
            20                  25                  30

Leu Trp Gly His Asp Pro Glu His Ile Ala Thr Leu Glu Arg Asp Arg
        35                  40                  45

Cys Asn Ala Ala Phe Leu Pro Asp Val Pro Phe Pro Asp Thr Leu His
    50                  55                  60

Leu Glu Ser Asp Leu Ala Thr Ala Leu Ala Ser Arg Asn Ile Leu
65                  70                  75                  80

Val Val Val Pro Ser His Val Phe Gly Glu Val Leu Arg Gln Ile Lys
                85                  90                  95

Pro Leu Met Arg Pro Asp Ala Arg Leu Val Trp Ala Thr Lys Gly Leu
            100                 105                 110

Glu Ala Glu Thr Gly Arg Leu Leu Gln Asp Val Ala Arg Glu Ala Leu
            115                 120                 125

Gly Asp Gln Ile Pro Leu Ala Val Ile Ser Gly Pro Thr Phe Ala Lys
        130                 135                 140

Glu Leu Ala Ala Gly Leu Pro Thr Ala Ile Ser Leu Ala Ser Thr Asp
145                 150                 155                 160

Gln Thr Phe Ala Asp Asp Leu Gln Gln Leu Leu His Cys Gly Lys Ser
                165                 170                 175

Phe Arg Val Tyr Ser Asn Pro Asp Phe Ile Gly Val Gln Leu Gly Gly
            180                 185                 190

Ala Val Lys Asn Val Ile Ala Ile Gly Ala Gly Met Ser Asp Gly Ile
            195                 200                 205

Gly Phe Gly Ala Asn Ala Arg Thr Ala Leu Ile Thr Arg Gly Leu Ala
        210                 215                 220

Glu Met Ser Arg Leu Gly Ala Ala Leu Gly Ala Asp Pro Ala Thr Phe
225                 230                 235                 240

Met Gly Met Ala Gly Leu Gly Asp Leu Val Leu Thr Cys Thr Glu Asn
                245                 250                 255

Gln Ser Arg Asn Arg Arg Phe Gly Met Met Leu Gly Gln Gly Met Asp
            260                 265                 270

Val Gln Ser Ala Gln Glu Lys Ile Gly Gln Val Val Glu Gly Tyr Arg
        275                 280                 285

Asn Thr Lys Glu Val Arg Glu Leu Ala His Arg Phe Gly Val Glu Met
        290                 295                 300

Pro Ile Thr Glu Glu Ile Tyr Gln Val Leu Tyr Cys Gly Lys Asn Ala
305                 310                 315                 320

Arg Glu Ala Ala Leu Thr Leu Leu Gly Arg Ala Arg Lys Asp Glu Arg
                325                 330                 335

Ser Ser His

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: PCR primer
      GPSA3

<400> SEQUENCE: 3
ttagtggctg ctgcgctc                                                   18
```

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: PCR primer GPSA5

<400> SEQUENCE: 4
aacaatgaac caacgtaa                                                   18

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: PCR primer GPSA31

<400> SEQUENCE: 5
gagagctctt agtggctgct gcgctc                                          26

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: PCR primer GPSA51

<400> SEQUENCE: 6
gaagaaggat ccaacaatga accaacgtaa                                      30

<210> SEQ ID NO 7
<211> LENGTH: 1020
<212> TYPE: DNA
<213> ORGANISM: Shigella flexneri

<400> SEQUENCE: 7
atgaaccaac gtaatgcttc aatgactgtg atcggtgccg gctcgtacgg caccgctctt      60
gccattaccc tggcaagaaa tggccacgag gttgtcctct ggggccatga ccctgaacat     120
atcgcaacgc ttgaacgcga ccgctgtaac gccgcgtttc tccccgatgt gccttttccc     180
gatacgctcc atcttgaaag cgatctcgcc actgcgctgg cagccagtcg taatattctc     240
gtcgtcgtac ccagccatgt ctttggtgaa gtgctgcgcc agattaaacc gctgatgcgt     300
cctgatgcgc gtcggtgtg gcgaccaaa gggctggaag cggaaaccgg acgtctgtta      360
caggacgtgg cgcgtgaggc cttaggcgat caaattccgc tggcggttat ctctggccca     420
acgtttgcga aagaactggc ggcaggttta ccgacagcta tttcgctggc ctcgaccgat     480
cagacctttg ccgatgatct ccagcagctg ctgcactgcg gcaaaagttt ccgcgtttac     540
agcaacccgg atttcattgg cgtgcagctt ggcggcgcgg tgaaaaacgt cattgccatt     600
ggcgcgggga tgtctgacgg tatcggtttt ggtgcgaatg cgcgtacggc gctgatcacc     660
cgtgggctgg ctgaaatgtc gcgtcttggt gcggcgctgg gtgccgatcc tgccaccttt     720
atgggcatgg cggggctggg cgatctggtg cttacctgta ccgacaacca gtcgcgtaac     780
cgccgttttg gtatgatgct cggtcagggc atggatgtac aaagcgcgca ggagaagatt     840
ggtcaggtgg tggaaggcta ccgcaatacg aaagaagtcc gcgaactggc gcatcgcttc     900
ggcgttgaaa tgccaataac cgaggaaatt tatcaagtat tatattgcgg aaaaaacgcg     960
cgcgaggcag cattgacatt attaggtcgt gcacgcaagg acgagcgcag cagtcactaa    1020

<210> SEQ ID NO 8
<211> LENGTH: 339
<212> TYPE: PRT
<213> ORGANISM: Shigella flexneri

<400> SEQUENCE: 8

Met Asn Gln Arg Asn Ala Ser Met Thr Val Ile Gly Ala Gly Ser Tyr
1               5                   10                  15

Gly Thr Ala Leu Ala Ile Thr Leu Ala Arg Asn Gly His Glu Val Val
            20                  25                  30

Leu Trp Gly His Asp Pro Glu His Ile Ala Thr Leu Glu Arg Asp Arg
        35                  40                  45

Cys Asn Ala Ala Phe Leu Pro Asp Val Pro Phe Pro Asp Thr Leu His
    50                  55                  60

Leu Glu Ser Asp Leu Ala Thr Ala Leu Ala Ala Ser Arg Asn Ile Leu
65                  70                  75                  80

Val Val Val Pro Ser His Val Phe Gly Glu Val Leu Arg Gln Ile Lys
                85                  90                  95

Pro Leu Met Arg Pro Asp Ala Arg Leu Val Trp Ala Thr Lys Gly Leu
            100                 105                 110

Glu Ala Glu Thr Gly Arg Leu Leu Gln Asp Val Ala Arg Glu Ala Leu
        115                 120                 125

Gly Asp Gln Ile Pro Leu Ala Val Ile Ser Gly Pro Thr Phe Ala Lys
    130                 135                 140

Glu Leu Ala Ala Gly Leu Pro Thr Ala Ile Ser Leu Ala Ser Thr Asp
145                 150                 155                 160

Gln Thr Phe Ala Asp Asp Leu Gln Gln Leu Leu His Cys Gly Lys Ser
                165                 170                 175

Phe Arg Val Tyr Ser Asn Pro Asp Phe Ile Gly Val Gln Leu Gly Gly
            180                 185                 190

Ala Val Lys Asn Val Ile Ala Ile Gly Ala Gly Met Ser Asp Gly Ile
        195                 200                 205

Gly Phe Gly Ala Asn Ala Arg Thr Ala Leu Ile Thr Arg Gly Leu Ala
    210                 215                 220

Glu Met Ser Arg Leu Gly Ala Ala Leu Gly Ala Asp Pro Ala Thr Phe
225                 230                 235                 240

Met Gly Met Ala Gly Leu Gly Asp Leu Val Leu Thr Cys Thr Asp Asn
                245                 250                 255

Gln Ser Arg Asn Arg Arg Phe Gly Met Met Leu Gly Gln Gly Met Asp
            260                 265                 270

Val Gln Ser Ala Gln Glu Lys Ile Gly Gln Val Val Glu Gly Tyr Arg
        275                 280                 285

Asn Thr Lys Glu Val Arg Glu Leu Ala His Arg Phe Gly Val Glu Met
    290                 295                 300

Pro Ile Thr Glu Glu Ile Tyr Gln Val Leu Tyr Cys Gly Lys Asn Ala
305                 310                 315                 320

Arg Glu Ala Ala Leu Thr Leu Leu Gly Arg Ala Arg Lys Asp Glu Arg
                325                 330                 335

Ser Ser His

<210> SEQ ID NO 9
<211> LENGTH: 1006
<212> TYPE: DNA
<213> ORGANISM: Salmonella typhimurium

```
<400> SEQUENCE: 9
atgaaccaaa gtaatgcgtc aatgacagtc atcggtgccg gctcgtacgg caccgctctt        60
gccatcactc tggcgagaaa cggccaccag gttgtcctgt ggggccacga cccaaaacat       120
atcgcgaccc tggagcacga tcgctgcaac gtcgcgttcc ttcccgatgt gccttttccc       180
gatacgttac acctggaaag cgacttagca accgcgctgg cggccagtcg taacattctg       240
gtggtggtgc caagccatgt tttcagcgac gtgctgcggc agattaaacc gctgatgcgt       300
ccggatgcgc gtctggtatg ggcgaccaaa ggcctggaag cggaaacggg cgcctgttg        360 caggatgtcg ctcgcgaggc gttaggcgat caaatcccgc tggcggtgat ttccggtccg       420
acgttcgcta aagagctggc ggcgggtttg ccgacggcaa tctcgctggc ctcaaccgat       480
gagacctttg ccgacgatct ccagcaactg ttgcactgcg gaaaaagttt tcgcgtctat       540
atcaatgcgg attttatcgg cgtgcagctt ggcggcgcgg tgaaaaatgt gattgcgatt       600
ggcgcgggga tgtctgacgg catcggcttc ggcgcgaacg cccgcacggc gctaatcacg       660
cgtggactga ccgaaatgtc gcggcttggc gcagcgcttg gtgccgatcc cgccaccttt       720
atggggatgg cgggtttagg cgatctggtg ctgacctgta ccgacaacca gtcgcgcaac       780
cgtcgttttg gcatgatgct tggccagggc atggacgtta aaggcgcgca ggataagatt       840
ggccaggtgg tcgaaggcta tcgcaatacg aaagaagttc gtgaattggc gcaccgtttt       900
ggtgttgaaa tgccaataac cgaggaaatt tatcaagtat tgtattgcgg aaaaaacgcg       960
cgcgaggcag cattaacgtt attaggtcgc gcccgcaagg aagagc                     1006

<210> SEQ ID NO 10
<211> LENGTH: 339
<212> TYPE: PRT
<213> ORGANISM: Salmonella typhimurium

<400> SEQUENCE: 10

Met Asn Gln Ser Asn Ala Ser Met Thr Val Ile Gly Ala Gly Ser Tyr
1               5                   10                  15

Gly Thr Ala Leu Ala Ile Thr Leu Ala Arg Asn Gly His Gln Val Val
            20                  25                  30

Leu Trp Gly His Asp Pro Lys His Ile Ala Thr Leu Glu His Asp Arg
        35                  40                  45

Cys Asn Val Ala Phe Leu Pro Asp Val Pro Phe Pro Asp Thr Leu His
    50                  55                  60

Leu Glu Ser Asp Leu Ala Thr Ala Leu Ala Ala Ser Arg Asn Ile Leu
65                  70                  75                  80

Val Val Val Pro Ser His Val Phe Ser Asp Val Leu Arg Gln Ile Lys
                85                  90                  95

Pro Leu Met Arg Pro Asp Ala Arg Leu Val Trp Ala Thr Lys Gly Leu
            100                 105                 110

Glu Ala Glu Thr Gly Arg Leu Leu Gln Asp Val Ala Arg Glu Ala Leu
        115                 120                 125

Gly Asp Gln Ile Pro Leu Ala Val Ile Ser Gly Pro Thr Phe Ala Lys
    130                 135                 140

Glu Leu Ala Ala Gly Leu Pro Thr Ala Ile Ser Leu Ala Ser Thr Asp
145                 150                 155                 160

Glu Thr Phe Ala Asp Asp Leu Gln Gln Leu His Cys Gly Lys Ser
                165                 170                 175

Phe Arg Val Tyr Ile Asn Ala Asp Phe Ile Gly Val Gln Leu Gly Gly
            180                 185                 190
```

```
Ala Val Lys Asn Val Ile Ala Ile Gly Ala Gly Met Ser Asp Gly Ile
            195                 200                 205
Gly Phe Gly Ala Asn Ala Arg Thr Ala Leu Ile Thr Arg Gly Leu Thr
        210                 215                 220
Glu Met Ser Arg Leu Gly Ala Ala Leu Gly Ala Asp Pro Ala Thr Phe
225                 230                 235                 240
Met Gly Met Ala Gly Leu Gly Asp Leu Val Leu Thr Cys Thr Asp Asn
                245                 250                 255
Gln Ser Arg Asn Arg Arg Phe Gly Met Met Leu Gly Gln Gly Met Asp
            260                 265                 270
Val Lys Gly Ala Gln Asp Lys Ile Gly Gln Val Val Glu Gly Tyr Arg
        275                 280                 285
Asn Thr Lys Glu Val Arg Glu Leu Ala His Arg Phe Gly Val Glu Met
        290                 295                 300
Pro Ile Thr Glu Glu Ile Tyr Gln Val Leu Tyr Cys Gly Lys Asn Ala
305                 310                 315                 320
Arg Glu Ala Ala Leu Thr Leu Leu Gly Arg Ala Arg Lys Glu Glu Leu
                325                 330                 335
Ser Arg His

<210> SEQ ID NO 11
<211> LENGTH: 1006
<212> TYPE: DNA
<213> ORGANISM: Salmonella enterica

<400> SEQUENCE: 11
atgaaccaaa gtaatgcgtc aatgacagtc atcggtgccg gctcgtacgg caccgctctc      60
gccatcactc tggcgagaaa cggccaccag gttgtcctgt ggggccacga cccaaaacat     120
atcgcgaccc tggagcacga tcgctgcaac gtcgcgttcc ttcccgatgt gccttttccc     180
gatacgttac acctggaaag cgacttagca accgcgctgg cggccagtcg taacattctg     240
gtggtggtgc aagccatgt tttcagcgac gtgctgcggc agattaaacc gctgatgcgt      300
ccggatgcgc gtctggtatg gcgaccaaa ggcctggaag cggaaacggg cgcctgttg       360
caggatgtcg ctcgcgaggc gttaggcgat caaatcccgc tggcggtgat ttccggtccg     420
acgttcgcta aagagctggc ggcgggtttg ccgacggcaa tctcgctagc ctcaaccgat     480
gagaccttg ccgacgatct ccagcaactg ttgcactgcg gaaaaagttt tcgcgtctat      540
atcaatgcgg atttttatcg cgtgcagctt ggcggcgcgg tgaaaaacgt gattgcgatt     600
ggcgcgggga tgtctgacgg catcggcttc ggcgcgaacg cccgcacggc gctaatcacg     660
cgtggactga ccgaaatgtc gcggcttggc gcagcgcttg gtgccgatcc cgccacctttt    720
atggggatgg cgggtttagg cgatctggtg ctgacctgta ccgacaacca gtcgcgcaac     780
cgtcgttttg gcatgatgct tggccagggc atggacgtta aaggcgcgca ggataagatt     840
ggccaggtgg tcgaaggcta tcgcaatacg aaagaagttc gtgaattggc gcaccgttt     900
ggtgttgaaa tgccaataac cgaggaaatt tatcaagtat tgtattgcgg aaaaaacgcg     960
cgcgaggcag cattaacgtt attaggtcgc gcccgcaagg aagagc                   1006

<210> SEQ ID NO 12
<211> LENGTH: 339
<212> TYPE: PRT
<213> ORGANISM: Salmonella enterica
```

<400> SEQUENCE: 12

```
Met Asn Gln Ser Asn Ala Ser Met Thr Val Ile Gly Ala Gly Ser Tyr
1               5                   10                  15
Gly Thr Ala Leu Ala Ile Thr Leu Ala Arg Asn Gly His Gln Val Val
            20                  25                  30
Leu Trp Gly His Asp Pro Lys His Ile Ala Thr Leu Glu His Asp Arg
        35                  40                  45
Cys Asn Val Ala Phe Leu Pro Asp Val Pro Phe Pro Asp Thr Leu His
    50                  55                  60
Leu Glu Ser Asp Leu Ala Thr Ala Leu Ala Ala Ser Arg Asn Ile Leu
65                  70                  75                  80
Val Val Val Pro Ser His Val Phe Ser Asp Val Leu Arg Gln Ile Lys
                85                  90                  95
Pro Leu Met Arg Pro Asp Ala Arg Leu Val Trp Ala Thr Lys Gly Leu
            100                 105                 110
Glu Ala Glu Thr Gly Arg Leu Leu Gln Asp Val Ala Arg Glu Ala Leu
        115                 120                 125
Gly Asp Gln Ile Pro Leu Ala Val Ile Ser Gly Pro Thr Phe Ala Lys
    130                 135                 140
Glu Leu Ala Ala Gly Leu Pro Thr Ala Ile Ser Leu Ala Ser Thr Asp
145                 150                 155                 160
Glu Thr Phe Ala Asp Asp Leu Gln Gln Leu Leu His Cys Gly Lys Ser
                165                 170                 175
Phe Arg Val Tyr Ile Asn Ala Asp Phe Ile Gly Val Gln Leu Gly Gly
            180                 185                 190
Ala Val Lys Asn Val Ile Ala Ile Gly Ala Gly Met Ser Asp Gly Ile
        195                 200                 205
Gly Phe Gly Ala Asn Ala Arg Thr Ala Leu Ile Thr Arg Gly Leu Thr
    210                 215                 220
Glu Met Ser Arg Leu Gly Ala Ala Leu Gly Ala Asp Pro Ala Thr Phe
225                 230                 235                 240
Met Gly Met Ala Gly Leu Gly Asp Leu Val Leu Thr Cys Thr Asp Asn
                245                 250                 255
Gln Ser Arg Asn Arg Arg Phe Gly Met Met Leu Gly Gln Gly Met Asp
            260                 265                 270
Val Lys Gly Ala Gln Asp Lys Ile Gly Gln Val Val Glu Gly Tyr Arg
        275                 280                 285
Asn Thr Lys Glu Val Arg Glu Leu Ala His Arg Phe Gly Val Glu Met
    290                 295                 300
Pro Ile Thr Glu Glu Ile Tyr Gln Val Leu Tyr Cys Gly Lys Asn Ala
305                 310                 315                 320
Arg Glu Ala Ala Leu Thr Leu Leu Gly Arg Ala Arg Lys Glu Glu Leu
                325                 330                 335
Ser Arg His
```

<210> SEQ ID NO 13
<211> LENGTH: 1020
<212> TYPE: DNA
<213> ORGANISM: Yersinia pestis

<400> SEQUENCE: 13

```
atgaacacca accctgcttc aatggctgtt atcggtgccg gatcttacgg caccgcatta      60
gctatcacac tggcgcgtaa tggccatcaa gtcgtgttat ggggccatga ccctaaacat     120
```

-continued

```
attcaacagc tgcaacaaga ccgctgtaac cgcgctttcc tacctgatgc tgctttcccc    180
gatacgttgc gattggaaac cgacttagca tgtgcgttgg ctgccagccg cgatgtgttg    240
gtcgtcgtgc ccagccatgt ctttggtgct gttttacatc agttgaagcc tcatctacgt    300
aaagatgcac gtatcgtctg gcaaccaaa gggctagaag ctgaaaccgg ccgtctgcta    360
caggatgtgg cccgcgaagt cttgggcgag ctatcccgc ttgccgtgat ttctggtcca    420
acgtttgcca aagaattggc cgcggggttt cctacggcga ttgcgttggc atcgaccgat    480
gtgcaattta gcgaagatct gcaacagtta ttgcactgtg gaaaaagctt tcgagtttac    540
agtaatcctg attttatcgg ggtacagctt ggtggcgcag tgaaaaacgt gattgccatc    600
ggtgcaggta tgtccgatgg catcggtttt ggtgcgaatg cccgtaccgc tctaataacc    660
cgcgggttag cggagatgac cgcgcttaggg acggcattag gtgccgatcc ttccacctt    720
atgggcatgg cagggttagg cgatttggtg ctaacctgca cagataacca atcccgtaac    780
cgccgatttg gcattatgct gggtcagggg ttggggtga aggaggcgca ggacaacatt    840
ggtcaagtgg tagaaggtta ccgtaatacc aaggaagttc tggcattagc acagcgtcat    900
ggcgtcgaaa tgccaataac tgaacaaatt tatcaagtgt tgtattgtca taagaatgct    960
cgtgaggcgg ctctgacgtt gttggggcgg accaaaaaag atgaaaaaat cggcatttga   1020
```

<210> SEQ ID NO 14
<211> LENGTH: 339
<212> TYPE: PRT
<213> ORGANISM: Yersinia pestis

<400> SEQUENCE: 14

```
Met Asn Thr Asn Pro Ala Ser Met Ala Val Ile Gly Ala Gly Ser Tyr
  1               5                  10                  15

Gly Thr Ala Leu Ala Ile Thr Leu Ala Arg Asn Gly His Gln Val Val
             20                  25                  30

Leu Trp Gly His Asp Pro Lys His Ile Gln Gln Leu Gln Gln Asp Arg
         35                  40                  45

Cys Asn Arg Ala Phe Leu Pro Asp Ala Ala Phe Pro Asp Thr Leu Arg
     50                  55                  60

Leu Glu Thr Asp Leu Ala Cys Ala Leu Ala Ala Ser Arg Asp Val Leu
 65                  70                  75                  80

Val Val Val Pro Ser His Val Phe Gly Ala Val Leu His Gln Leu Lys
                 85                  90                  95

Pro His Leu Arg Lys Asp Ala Arg Ile Val Trp Ala Thr Lys Gly Leu
            100                 105                 110

Glu Ala Glu Thr Gly Arg Leu Leu Gln Asp Val Ala Arg Glu Val Leu
        115                 120                 125

Gly Glu Ala Ile Pro Leu Ala Val Ile Ser Gly Pro Thr Phe Ala Lys
    130                 135                 140

Glu Leu Ala Ala Gly Leu Pro Thr Ala Ile Ala Leu Ala Ser Thr Asp
145                 150                 155                 160

Val Gln Phe Ser Glu Asp Leu Gln Gln Leu Leu His Cys Gly Lys Ser
                165                 170                 175

Phe Arg Val Tyr Ser Asn Pro Asp Phe Ile Gly Val Gln Leu Gly Gly
            180                 185                 190

Ala Val Lys Asn Val Ile Ala Ile Gly Ala Gly Met Ser Asp Gly Ile
        195                 200                 205

Gly Phe Gly Ala Asn Ala Arg Thr Ala Leu Ile Thr Arg Gly Leu Ala
    210                 215                 220
```

```
Glu Met Thr Arg Leu Gly Thr Ala Leu Gly Ala Asp Pro Ser Thr Phe
225                 230                 235                 240

Met Gly Met Ala Gly Leu Gly Asp Leu Val Leu Thr Cys Thr Asp Asn
            245                 250                 255

Gln Ser Arg Asn Arg Arg Phe Gly Ile Met Leu Gly Gln Gly Leu Gly
        260                 265                 270

Val Lys Glu Ala Gln Asp Asn Ile Gly Gln Val Val Glu Gly Tyr Arg
    275                 280                 285

Asn Thr Lys Glu Val Leu Ala Leu Ala Gln Arg His Gly Val Glu Met
        290                 295                 300

Pro Ile Thr Glu Gln Ile Tyr Gln Val Leu Tyr Cys His Lys Asn Ala
305                 310                 315                 320

Arg Glu Ala Ala Leu Thr Leu Leu Gly Arg Thr Lys Lys Asp Glu Lys
                325                 330                 335

Ile Gly Ile

<210> SEQ ID NO 15
<211> LENGTH: 1020
<212> TYPE: DNA
<213> ORGANISM: Yersinia pseudotuberculosis

<400> SEQUENCE: 15
atgaacacca accctgcttc aatggctgtt atcggtgccg gatcttacgg caccgcatta      60
gctatcacac tggcgcgtaa tggccatcaa gtcgtgttat gggccatgaa ccctaaacat     120
attcaacagc tgcaacaaga ccgctgtaac cgcgctttcc tacctgatgc tgctttcccc     180
gatacgttgc gattggaaac cgacttagca tgtgcgttgg ctgccagccg cgatgtgttg     240
gtcgtcgtgc ccagccatgt ctttggtgct gttttacatc agttgaagcc tcatctacgt     300
aaagatgcac gtatcgtctg ggcaaccaaa gggctagaag ctgaaaccgg ccgtctgcta     360
caggatgtgg cccgcgaagt cttgggcgag gctatcccgc ttgccgtgat ttctggtcca     420
acgtttgcca agaattggcg cgcggggttg cctacggcga ttgcgttggc atcgaccgat     480
gtgcaattta gcgaagatct gcaacagtta ttgcactgtg aaaaagcttt cgagtttac     540
agtaatcctg attttatcgg ggtacagctt ggtggcgcag tgaaaaacgt gattgccatc     600
ggtgcaggta tgtccgatgg catcggtttt ggtgcgaatg cccgtaccgc tctaataacc     660
cgcgggttag cggagatgac gcgcttaggg acggcattag gtgccgatcc ttccaccttt     720
atgggcatgg cagggttagg cgatttggtg ctaacctgca cagataacca atcccgtaac     780
cgccgatttg gcattatgct gggtcagggg ttgggggtga aggaggcgca ggacaacatt     840
ggtcaagtgg tagaaggtta ccgtaatacc aaggaagttc tggcattagc acagcgtcat     900
ggcgtcgaaa tgccaataac tgaacaaatt tatcaagtgt tgtattgtca taagaatgct     960
cgtgaggcgg ctctgacgtt gttggggcgg accaaaaaag atgaaaaaat cggcatttga    1020

<210> SEQ ID NO 16
<211> LENGTH: 339
<212> TYPE: PRT
<213> ORGANISM: Yersinia pseudotuberculosis

<400> SEQUENCE: 16

Met Asn Thr Asn Pro Ala Ser Met Ala Val Ile Gly Ala Gly Ser Tyr
1               5                   10                  15

Gly Thr Ala Leu Ala Ile Thr Leu Ala Arg Asn Gly His Gln Val Val
            20                  25                  30
```

```
Leu Trp Gly His Asp Pro Lys His Ile Gln Gln Leu Gln Gln Asp Arg
        35                  40                  45

Cys Asn Arg Ala Phe Leu Pro Asp Ala Ala Phe Pro Asp Thr Leu Arg
 50                  55                  60

Leu Glu Thr Asp Leu Ala Cys Ala Leu Ala Ala Ser Arg Asp Val Leu
 65                  70                  75                  80

Val Val Val Pro Ser His Val Phe Gly Ala Val Leu His Gln Leu Lys
                 85                  90                  95

Pro His Leu Arg Lys Asp Ala Arg Ile Val Trp Ala Thr Lys Gly Leu
             100                 105                 110

Glu Ala Glu Thr Gly Arg Leu Leu Gln Asp Val Ala Arg Glu Val Leu
         115                 120                 125

Gly Glu Ala Ile Pro Leu Ala Val Ile Ser Gly Pro Thr Phe Ala Lys
130                 135                 140

Glu Leu Ala Ala Gly Leu Pro Thr Ala Ile Ala Leu Ala Ser Thr Asp
145                 150                 155                 160

Val Gln Phe Ser Glu Asp Leu Gln Gln Leu Leu His Cys Gly Lys Ser
                165                 170                 175

Phe Arg Val Tyr Ser Asn Pro Asp Phe Ile Gly Val Gln Leu Gly Gly
            180                 185                 190

Ala Val Lys Asn Val Ile Ala Ile Gly Ala Gly Met Ser Asp Gly Ile
        195                 200                 205

Gly Phe Gly Ala Asn Ala Arg Thr Ala Leu Ile Thr Arg Gly Leu Ala
    210                 215                 220

Glu Met Thr Arg Leu Gly Thr Ala Leu Gly Ala Asp Pro Ser Thr Phe
225                 230                 235                 240

Met Gly Met Ala Gly Leu Gly Asp Leu Val Leu Thr Cys Thr Asp Asn
                245                 250                 255

Gln Ser Arg Asn Arg Arg Phe Gly Ile Met Leu Gly Gln Gly Leu Gly
            260                 265                 270

Val Lys Glu Ala Gln Asp Asn Ile Gly Gln Val Val Glu Gly Tyr Arg
        275                 280                 285

Asn Thr Lys Glu Val Leu Ala Leu Ala Gln Arg His Gly Val Glu Met
    290                 295                 300

Pro Ile Thr Glu Gln Ile Tyr Gln Val Leu Tyr Cys His Lys Asn Ala
305                 310                 315                 320

Arg Glu Ala Ala Leu Thr Leu Leu Gly Arg Thr Lys Lys Asp Glu Lys
                325                 330                 335

Ile Gly Ile

<210> SEQ ID NO 17
<211> LENGTH: 1023
<212> TYPE: DNA
<213> ORGANISM: Serratia marcescens

<400> SEQUENCE: 17
atgaacaccg tcaatgcttc aatgactgtt atcggtgccg gctcgtacgg caccgcattg      60
gccattacgc tggcgcgtaa cggccattcc gtggtgctgt gggggcacaa ccccgcgcaa     120
attcaaacgt tgcagcacga tcgctgcaat caggcgtttc tgcccgacgt tcccttcccc     180
gataccctgc tgcttgaagc cgatttggcg cgtgcgctgg ccgccagccg cgacgtgctg     240
gtggtggtgc cgagccacgt gttcggcgac gtgctgcgcc agctgaagcc gcatctgcgc     300
ccggacgccc gcatcgtgtg ggccaccaag ggattggaag cggaaaccgg tcggttgctg     360
```

-continued

```
cagaacgtgg cgcgtgaggc gctgggcgag acgatcccgc tggcggtgct ctccgggccg    420
acgttcgcca aagagctggc cgccggcctg ccgacggcga tcgcgctggc ggcgaccgat    480
gcgcagttcg ccgacgatct gcaacagggc tgcatgcact gcggcaagag cttccgtgtc    540
tacagcaatc ccgacttcat cggcgtgcag cttggcggcg cggtgaagaa cgtgatcgcc    600
atcggcgccg gcatgtccga cggcatcggt tcggcgcta acgcccgtac cgcgttgatt    660
acacgcgggc tggcggaaat gagccgtctg ggttctgcgc tgggcgccga tccttcgacg    720
ttcatgggca tggcggggct gggggatctg gtgctaacct gcacggacaa ccagtcgcgc    780
aaccgtcgct tcggcattat gctggggcag ggtaaaggcg tgcaggaagc gcaggacagt    840
atcggtcagg tggtcgaggg ctatcgcaat accaaagagg tgttggcgtt ggcgcagcgg    900
cagggtgtgg aaatgccgat caccgaacag atttatcagg tgctttactg ccacaaggac    960 gccccgcgaag cggcgctgag cctgctgggg cgagcccgaa aggacgaaaa acccagcgtg   1020
tga                                                                 1023
```

<210> SEQ ID NO 18
<211> LENGTH: 340
<212> TYPE: PRT
<213> ORGANISM: Serratia marcescens

<400> SEQUENCE: 18

```
Met Asn Thr Val Asn Ala Ser Met Thr Val Ile Gly Ala Gly Ser Tyr
 1               5                  10                  15

Gly Thr Ala Leu Ala Ile Thr Leu Ala Arg Asn Gly His Ser Val Val
             20                  25                  30

Leu Trp Gly His Asn Pro Ala Gln Ile Gln Thr Leu Gln His Asp Arg
         35                  40                  45

Cys Asn Gln Ala Phe Leu Pro Asp Val Pro Phe Pro Asp Thr Leu Leu
     50                  55                  60

Leu Glu Ala Asp Leu Ala Arg Ala Leu Ala Ala Ser Arg Asp Val Leu
 65                  70                  75                  80

Val Val Val Pro Ser His Val Phe Gly Asp Val Leu Arg Gln Leu Lys
                 85                  90                  95

Pro His Leu Arg Pro Asp Ala Arg Ile Val Trp Ala Thr Lys Gly Leu
            100                 105                 110

Glu Ala Glu Thr Gly Arg Leu Leu Gln Asn Val Ala Arg Glu Ala Leu
        115                 120                 125

Gly Glu Thr Ile Pro Leu Ala Val Leu Ser Gly Pro Thr Phe Ala Lys
    130                 135                 140

Glu Leu Ala Ala Gly Leu Pro Thr Ala Ile Ala Leu Ala Ala Thr Asp
145                 150                 155                 160

Ala Gln Phe Ala Asp Asp Leu Gln Gln Gly Cys Met His Cys Gly Lys
                165                 170                 175

Ser Phe Arg Val Tyr Ser Asn Pro Asp Phe Ile Gly Val Gln Leu Gly
            180                 185                 190

Gly Ala Val Lys Asn Val Ile Ala Ile Gly Ala Gly Met Ser Asp Gly
        195                 200                 205

Ile Gly Phe Gly Ala Asn Ala Arg Thr Ala Leu Ile Thr Arg Gly Leu
    210                 215                 220

Ala Glu Met Ser Arg Leu Gly Ser Ala Leu Gly Ala Asp Pro Ser Thr
225                 230                 235                 240

Phe Met Gly Met Ala Gly Leu Gly Asp Leu Val Leu Thr Cys Thr Asp
                245                 250                 255
```

Asn Gln Ser Arg Asn Arg Arg Phe Gly Ile Met Leu Gly Gln Gly Lys
                260                 265                 270

Gly Val Gln Glu Ala Gln Asp Ser Ile Gly Gln Val Val Glu Gly Tyr
            275                 280                 285

Arg Asn Thr Lys Glu Val Leu Ala Leu Ala Gln Arg Gln Gly Val Glu
        290                 295                 300

Met Pro Ile Thr Glu Gln Ile Tyr Gln Val Leu Tyr Cys His Lys Asp
305                 310                 315                 320

Ala Arg Glu Ala Ala Leu Ser Leu Leu Gly Arg Ala Arg Lys Asp Glu
                325                 330                 335

Lys Pro Ser Val
            340

<210> SEQ ID NO 19
<211> LENGTH: 1052
<212> TYPE: DNA
<213> ORGANISM: Photorhabdus luminescens

<400> SEQUENCE: 19
atgaatagta ctgtttctat gacagtgatt ggtgccggct catacggcac ctcattagcc        60
attacgctgg ctcgtaatgg tcataatgtt gtactttggg gcataatcc agagcatgtt       120
ggggcattgc aacgggtgcg ttgtaatcaa aaatttctgc cggatgtttc ctttcctgat       180
agtttattgc ttgaaacgga cctaataaaa gcactaacag cgagccgcga tattcttgtt       240
gtggtaccta gccatgtgtt tggtgaagtg ttaaagcaga taaaaccaca tttacggcct       300
gattcacgta tcgtatgggc aactaaaggc ttggaagcgg ataccggtcg ttattgcag        360
gatgtggccc gtgagatatt aggcaatgaa ataccgctag cggtgctctc tgggccaaca       420
tttgctaaag agttagcggc tggtttgcct accgcgattg ctatttccgc gacggaatct       480
gcttttggcg atggacttca acaattattc cactgtggca aaagtttccg ggtttataaa       540
atcctgatt ttattggtgt tcaactcggt ggtgccgtaa aaaacgtgat cgccattggc       600
gcgggaatat ctgatggcat gggatttggt gctaatgctc gtaccgcatt gattactcgt       660
ggattggcgg aaatgagtcg ccttggtgca gcgcttggtg ctgatccttc taccttatg       720
ggcatggcgg gattgggcga tttggtctta acttgtactg ataaccaatc acgtaaccgt       780
cgttttggca tgatgctggg gcagggaatc agtgttgaag aagcgcagta tcagattggg       840
caggttgttg aaggttatcg caataccaaa gaagtacgtg cattggctaa tcgcgccaat       900
gtagaaatgc cgattgcaga acaaatctac cagatactct attgcaataa aaatgtgata       960
gaagctgctc aggcattatt aggaagagcc agaaaggatg agagcgataa tgtgcgctct      1020
taaataaaaa tctaatgaga taggttctaa tg                                    1052

<210> SEQ ID NO 20
<211> LENGTH: 340
<212> TYPE: PRT
<213> ORGANISM: Photorhabdus luminescens

<400> SEQUENCE: 20

Met Asn Ser Thr Val Ser Met Thr Val Ile Gly Ala Gly Ser Tyr Gly
1               5                   10                  15

Thr Ser Leu Ala Ile Thr Leu Ala Arg Asn Gly His Asn Val Val Leu
            20                  25                  30

Trp Gly His Asn Pro Glu His Val Gly Ala Leu Gln Arg Val Arg Cys
        35                  40                  45

-continued

```
Asn Gln Lys Phe Leu Pro Asp Val Ser Phe Pro Asp Ser Leu Leu Leu
    50                  55                  60

Glu Thr Asp Leu Ile Lys Ala Leu Thr Ala Ser Arg Asp Ile Leu Val
65                  70                  75                  80

Val Val Pro Ser His Val Phe Gly Glu Val Leu Lys Gln Ile Lys Pro
                85                  90                  95

His Leu Arg Pro Asp Ser Arg Ile Val Trp Ala Thr Lys Gly Leu Glu
            100                 105                 110

Ala Asp Thr Gly Arg Leu Leu Gln Asp Val Ala Arg Glu Ile Leu Gly
        115                 120                 125

Asn Glu Ile Pro Leu Ala Val Leu Ser Gly Pro Thr Phe Ala Lys Glu
    130                 135                 140

Leu Ala Ala Gly Leu Pro Thr Ala Ile Ala Ile Ser Ala Thr Glu Ser
145                 150                 155                 160

Ala Phe Gly Asp Gly Leu Gln Gln Leu Phe His Cys Gly Lys Ser Phe
                165                 170                 175

Arg Val Tyr Lys Asn Pro Asp Phe Ile Gly Val Gln Leu Gly Gly Ala
            180                 185                 190

Val Lys Asn Val Ile Ala Ile Gly Ala Gly Ile Ser Asp Gly Met Gly
        195                 200                 205

Phe Gly Ala Asn Ala Arg Thr Ala Leu Ile Thr Arg Gly Leu Ala Glu
    210                 215                 220

Met Ser Arg Leu Gly Ala Ala Leu Gly Ala Asp Pro Ser Thr Phe Met
225                 230                 235                 240

Gly Met Ala Gly Leu Gly Asp Leu Val Leu Thr Cys Thr Asp Asn Gln
                245                 250                 255

Ser Arg Asn Arg Arg Phe Gly Met Met Leu Gly Gln Gly Ile Ser Val
            260                 265                 270

Glu Glu Ala Gln Tyr Gln Ile Gly Gln Val Val Glu Gly Tyr Arg Asn
        275                 280                 285

Thr Lys Glu Val Arg Ala Leu Ala Asn Arg Ala Asn Val Glu Met Pro
    290                 295                 300

Ile Ala Glu Gln Ile Tyr Gln Ile Leu Tyr Cys Asn Lys Asn Val Ile
305                 310                 315                 320

Glu Ala Ala Gln Ala Leu Leu Gly Arg Ala Arg Lys Asp Glu Ser Asp
                325                 330                 335

Asn Val Arg Ser
            340

<210> SEQ ID NO 21
<211> LENGTH: 1020
<212> TYPE: DNA
<213> ORGANISM: Erwinia carotovora

<400> SEQUENCE: 21
atgaacgcgt ctgacgcttc catgaccgtc atcggtgccg gttcatacgg caccgcatta      60
gccattacgc tggcgcgtaa tggccatcga gtcgtgctgt ggggtcacaa ccctacgcac     120
attcaggcct tacaggccgc tcgttgtaat caggcattcc tgccggatgt ccctttcccc     180
gattcgctac agttggaaac taatctggct catgcgctcg ctgccagtag aaacgtgctg     240
gttgtcgtgc cgagccatgt attcggcgat gttttgcgtc agttgaaacc tcatttgcgt     300
gccgatgcac gtatcgtgtg ggcgaccaaa gggctggaag cagaaacggg gcgtctgttg     360
caggatgtcg cacgcgaagc gttgggtgaa accatcccgc ttgcggtggt atctggcccg     420
```

-continued

```
acatttgcca aagaattagc ggccggcatg ccgacggcta ttgctctggc atcaccggac    480
agtgaatttg ctgacgacct gcaacagcta ctgcattgcg ggaagagctt ccgtgtttac    540
agcaacccag attttatcgg cgtgcagttg ggcggagcgg tgaaaaacgt cattgctatc    600
ggtgctggga tgtctgacgg cattgggttt ggtgctaatg cacgtactgc attgatcacc    660
cgcgggctgg cagaaatgac ccggcttggt gcagcactgg gcgcggatcc tactaccttc    720
atggggatgg ctgggcttgg cgatttggtg ctgacctgta ctgataatca gtcccgtaac    780
cgacgctttg gcatgatgct ggggcaggga atggacgtgc agagcgcaca ggatagcatt    840
ggtcaggttg ttgaaggata ccgcaatacg aaagaagtat tggcattagc acagcgctac    900
ggcgttgaaa tgccgattac ggagcaactc tggcaggttc tgtattgtgg gaaagacgcc    960
cgcgaggcgg cgttaagcct attggggcga acgcgtaaag acgaaaccgc caaattataa   1020
```

<210> SEQ ID NO 22
<211> LENGTH: 339
<212> TYPE: PRT
<213> ORGANISM: Erwinia carotovora

<400> SEQUENCE: 22

```
Met Asn Ala Ser Asp Ala Ser Met Thr Val Ile Gly Ala Gly Ser Tyr
1               5                   10                  15

Gly Thr Ala Leu Ala Ile Thr Leu Ala Arg Asn Gly His Arg Val Val
            20                  25                  30

Leu Trp Gly His Asn Pro Thr His Ile Gln Ala Leu Gln Ala Ala Arg
        35                  40                  45

Cys Asn Gln Ala Phe Leu Pro Asp Val Pro Phe Pro Asp Ser Leu Gln
    50                  55                  60

Leu Glu Thr Asn Leu Ala His Ala Leu Ala Ala Ser Arg Asn Val Leu
65                  70                  75                  80

Val Val Val Pro Ser His Val Phe Gly Asp Val Leu Arg Gln Leu Lys
                85                  90                  95

Pro His Leu Arg Ala Asp Ala Arg Ile Val Trp Ala Thr Lys Gly Leu
            100                 105                 110

Glu Ala Glu Thr Gly Arg Leu Leu Gln Asp Val Ala Arg Glu Ala Leu
        115                 120                 125

Gly Glu Thr Ile Pro Leu Ala Val Val Ser Gly Pro Thr Phe Ala Lys
    130                 135                 140

Glu Leu Ala Ala Gly Met Pro Thr Ala Ile Ala Leu Ala Ser Pro Asp
145                 150                 155                 160

Ser Glu Phe Ala Asp Asp Leu Gln Gln Leu Leu His Cys Gly Lys Ser
                165                 170                 175

Phe Arg Val Tyr Ser Asn Pro Asp Phe Ile Gly Val Gln Leu Gly Gly
            180                 185                 190

Ala Val Lys Asn Val Ile Ala Ile Gly Ala Gly Met Ser Asp Gly Ile
        195                 200                 205

Gly Phe Gly Ala Asn Ala Arg Thr Ala Leu Ile Thr Arg Gly Leu Ala
    210                 215                 220

Glu Met Thr Arg Leu Gly Ala Ala Leu Gly Ala Asp Pro Thr Thr Phe
225                 230                 235                 240

Met Gly Met Ala Gly Leu Gly Asp Leu Val Leu Thr Cys Thr Asp Asn
                245                 250                 255

Gln Ser Arg Asn Arg Arg Phe Gly Met Met Leu Gly Gln Gly Met Asp
            260                 265                 270
```

-continued

```
Val Gln Ser Ala Gln Asp Ser Ile Gly Gln Val Val Glu Gly Tyr Arg
        275                 280                 285

Asn Thr Lys Glu Val Leu Ala Leu Ala Gln Arg Tyr Gly Val Glu Met
        290                 295                 300

Pro Ile Thr Glu Gln Leu Trp Gln Val Leu Tyr Cys Gly Lys Asp Ala
305                 310                 315                 320

Arg Glu Ala Ala Leu Ser Leu Leu Gly Arg Thr Arg Lys Asp Glu Thr
                325                 330                 335

Ala Lys Leu
```